(12) United States Patent
Zannoni et al.

(10) Patent No.: US 10,821,061 B2
(45) Date of Patent: *Nov. 3, 2020

(54) LIQUID COMPOSITIONS FOR HAIR REMOVAL DEVICES COMPRISING METATHESIZED UNSATURATED POLYOL ESTERS

(71) Applicant: The Gillette Company LLC, Boston, MA (US)

(72) Inventors: Luke Andrew Zannoni, West Chester, OH (US); Beth Ann Schubert, Mainville, OH (US); Rajan Keshav Panandiker, West Chester, OH (US); Joseph Jay Kemper, Cincinnati, OH (US); Robert John Strife, West Chester, OH (US); Safa Motlagh, Dayton, OH (US); Jeffrey John Scheibel, Glendale, OH (US); Alison Fiona Stephens, Maidenhead (GB); Philip Andrew Sawin, Cincinnati, OH (US)

(73) Assignee: The Gillette Company LLC, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/643,934

(22) Filed: Jul. 7, 2017

(65) Prior Publication Data

US 2018/0008520 A1 Jan. 11, 2018

Related U.S. Application Data

(60) Provisional application No. 62/359,790, filed on Jul. 8, 2016.

(51) Int. Cl.
| | | |
|---|---|---|
| *A61K 8/37* | (2006.01) | |
| *C10M 111/04* | (2006.01) | |
| *A45D 27/00* | (2006.01) | |
| *C11C 3/10* | (2006.01) | |
| *C10M 173/02* | (2006.01) | |
| *C11C 3/00* | (2006.01) | |
| *C10M 109/02* | (2006.01) | |
| *C10M 173/00* | (2006.01) | |
| *C10M 105/38* | (2006.01) | |
| *A45D 34/04* | (2006.01) | |
| *A61K 8/81* | (2006.01) | |
| *A61K 8/92* | (2006.01) | |
| *A61Q 9/02* | (2006.01) | |
| *C08K 5/103* | (2006.01) | |
| *C10N 10/02* | (2006.01) | |
| *C10N 20/04* | (2006.01) | |
| *C10N 40/06* | (2006.01) | |

(52) U.S. Cl.
CPC ............ *A61K 8/37* (2013.01); *A45D 27/00* (2013.01); *A45D 34/04* (2013.01); *A61K 8/8111* (2013.01); *A61K 8/922* (2013.01); *A61Q 9/02* (2013.01); *C08K 5/103* (2013.01); *C10M 105/38* (2013.01); *C10M 109/02* (2013.01); *C10M 111/04* (2013.01); *C10M 173/00* (2013.01); *C10M 173/02* (2013.01); *C11C 3/00* (2013.01); *C11C 3/10* (2013.01); *A45D 2200/056* (2013.01); *A45D 2200/1036* (2013.01); *A61K 2800/87* (2013.01); *C10M 2207/022* (2013.01); *C10M 2207/04* (2013.01); *C10M 2207/08* (2013.01); *C10M 2207/2835* (2013.01); *C10M 2209/084* (2013.01); *C10M 2209/104* (2013.01); *C10M 2209/107* (2013.01); *C10M 2209/12* (2013.01); *C10M 2215/04* (2013.01); *C10M 2215/042* (2013.01); *C10M 2217/024* (2013.01); *C10M 2217/028* (2013.01); *C10M 2219/042* (2013.01); *C10N 2010/02* (2013.01); *C10N 2020/04* (2013.01); *C10N 2040/06* (2013.01)

(58) Field of Classification Search
CPC combination set(s) only.
See application file for complete search history.

(56) References Cited

U.S. PATENT DOCUMENTS

| | | | |
|---|---|---|---|
| 5,454,164 A | 10/1995 | Yin et al. | |
| 5,558,071 A * | 9/1996 | Ward | F02P 3/02 123/598 |
| 6,579,851 B2 * | 6/2003 | Goeke | A61K 38/26 514/11.7 |
| 8,461,129 B2 * | 6/2013 | Bolduc | A61L 15/28 127/49 |
| 8,815,257 B2 * | 8/2014 | Braksmayer | A23D 7/0053 424/400 |
| 1,003,969 A1 | 8/2018 | Braksmayer et al. | |
| 2009/0048459 A1* | 2/2009 | Tupy | C10G 45/00 554/146 |
| 2011/0028412 A1* | 2/2011 | Cappello | A61K 31/7004 514/25 |

(Continued)

OTHER PUBLICATIONS

Luke Andrew Zannoni et al.; Related U.S. Appl. No. 17/023,616 entitled "Liquid Compositions for Hair Removal Devices Comprising Metathesized Unsaturated Polyol Esters",filed Sep. 17, 2020.
PCT International Search Report with Written Opinion in corresponding Int'l appln. PCT/US2017/041017 dated Oct. 5, 2017.

(Continued)

*Primary Examiner* — Andrew S Rosenthal
(74) *Attorney, Agent, or Firm* — Kevin C. Johnson

(57) ABSTRACT

The invention relates to liquid compositions for use with hair removal devices comprising a methathesized unsaturated polyol ester for improved lubrication.

15 Claims, No Drawings

(56) References Cited

U.S. PATENT DOCUMENTS

| | | | |
|---|---|---|---|
| 2011/0219621 A1* | 9/2011 | Royle | B26B 21/446 30/41 |
| 2013/0041004 A1* | 2/2013 | Drager | A61K 9/08 514/394 |
| 2013/0084243 A1* | 4/2013 | Goetsch | C07K 16/2863 424/1.49 |
| 2013/0096073 A1* | 4/2013 | Sidelman | A61K 38/1709 514/21.6 |
| 2013/0280174 A1* | 10/2013 | Lipic | A61K 8/046 424/43 |
| 2013/0344012 A1* | 12/2013 | Cohen | C10G 3/42 424/59 |
| 2014/0255330 A1 | 9/2014 | Cron et al. | |

OTHER PUBLICATIONS

Univar: "Dow Corning HY-3050 Soy Wax", Internet Citation, Oct. 4, 2008 (Oct. 4, 2008). pp. 1-3, XP002727611. Retrieved from the Internet: URL:http://www.univar.com/US/Industries/'/media/PDFs/US%20Corp%20Region%2OPDFs/PC/Naturals/DC%2OHY-3050%20Soy%20Wax%20from%20Univar.ashx retrieved on Jul. 22, 2014.
"Elevance Soft CG-100", Sep. 13, 2011 (Sep. 13, 2011), pp. 1-2, XP055130964, Retrieved from the Internet: URL:http://www.elevance.com/documents/technical/Elevance-CG-100-Soy-Wax-Blend-Technical-Data.pdf [retrieved on Jul. 22, 2014].

* cited by examiner

LIQUID COMPOSITIONS FOR HAIR REMOVAL DEVICES COMPRISING METATHESIZED UNSATURATED POLYOL ESTERS

FIELD OF THE INVENTION

The invention relates to liquid compositions comprising metathesized unsaturated polyol esters exhibiting improved lubricating properties and their use in hair removal devices.

BACKGROUND OF THE INVENTION

The use of solid shaving aids or liquid compositions with hair removal devices before or during the shaving process to provide lubrication benefits is known in the art. Lubricating members are typically located on the razor cartridge and release the actives upon contact with water during the shaving process. Alternatively, lubrication may be delivered by the use of liquid or foaming shaving compositions applied before the shaving process or contained within the razor handle and which are dispensed during shaving by activation by the user. Foaming shaving compositions are described for example in WO91/07943, DE10201321980 and GB1299089.

However, since the introduction of polyethylene oxide (polyox) as a shaving lubricant as described in the art above for example, little development has been made in the field, even though polyethylene oxide polymers are not without limitations. For example, utilizing polyethylene oxide polymers having low molecular weights or high molecular weights may improve may provide a means to improve lubrication, but may also result in trade off with regard to residue and or stringiness or other aspects of the aqueous solution typically formed in-use. For example, the resultant viscosity in aqueous solution may also increase, leading to negatively perceived attributes, for example concerning the feeling of the shave for the user, particularly in respect of the lubricant. The prior art does also describe the use of combinations of high and low molecular weight polyethylene oxide polymers in order to balance these performance attributes. Nevertheless, such combinations are also limited in their ability to improve performance and or suffer from other negative performance attributes.

The solid shaving aid art further describes the incorporation of additional materials such as oils to further improve the lubrication performance as described in for example U.S. Pat. No. 6,442,839, US2007/0110703 US2009/0223057, and US2008/0060201. However, such solid shaving aids exhibit a reduction of the swelling and solubility of water soluble shaving aid contained in the water insoluble polymer matrix. The ability of the shaving aid to swell in contact with water is however believed to be the key mechanism by which the lubrication benefit is delivered to the skin. Hence this is not desirable, as it will negatively impact the overall performance.

Several different composition dispensing razors are known in the art as described in e.g., U.S. Pat. Nos. 7,007,389, 6,308,413, 4,753,006, 4,635,361, 6,986,207, 5,855,066 and 4,129,942. Such dispensing razors have been described as being capable of dispensing various types of shaving related preparations, including clear or translucent shaving gels or lotions. Compositions intended for liquid dispensing in addition to providing lubrication also need to ensure the desired viscosity. For example, a less viscous formulation may be desirable in certain instances, such as where the formulator wants the composition to dispense in a discrete area but quickly spread to contact and/or coat a large surface, such as the shaving head and cutters. It can also be desirable, however, for the product to be sufficiently thick so it will not run off or otherwise be pushed away from the portion of skin desired for treatment. Many different types of thickeners and viscosity modifying agents can impact the viscosity and rheology of the composition. Many of these ingredients, however, also impact other characteristics of the composition when added, such as making the composition stringy or tacky, or making the composition cloudy or opaque which may not be desirable in certain embodiments.

One other class of ingredients which is known to provide lubrication benefits includes surfactants, particularly soaps. Many of these surfactants, however, are capable of causing undesirable skin irritation during and following use in certain instances, particularly in hard water areas. This can be particularly relevant where users do not wash off the composition from skin following the hair removal process, which may exacerbate skin irritation.

Consequently, there is still a need to provide a liquid composition to be utilized before or during shaving exhibiting improved lubricating properties which can be readily manufactured without impacting performance and which can be readily applied and left on the skin without causing negative skin impacts such as irritation or stringiness.

Metathesized unsaturated polyol esters have been described in the literature to improve the performance of foaming compositions as described for example in US2013/0280174. However, it has been now been surprisingly found that the metathesized unsaturated polyol esters described herein also improve the spreadability and lubrication of the liquid formulation during the shave and post shave skin attributes due to their targeted rheology. Additionally, their pH and salt tolerances allows combination with shave foams and gels without issue.

SUMMARY OF THE INVENTION

One aspect of the invention relates to a composition dispensing hair removal device, said device containing a liquid composition comprising from 0.1% to 60% by weight of metathesized unsaturated polyol esters having one or more of the following properties:
(i) a weight average molecular weight of from about 5,000 Daltons to about 50,000 Daltons;
(ii) an oligomer index from greater than 0 to 1;
(iii) an iodine value of from about 30 to about 200.

Another aspect of the invention relates to a composition dispensing hair removal device, said device comprising a composition comprising:
a) a metathesized unsaturated polyol ester, said metathesized unsaturated polyol ester having a weight average molecular weight of from about 2,000 Daltons to about 50,000 Daltons; and one or more of the following properties:
(i) a free hydrocarbon content, based on total weight of metathesized unsaturated polyol ester of from about 0% to about 5%;
(ii) an oligomer index from greater than 0 to 1;
(iii) an iodine value of from about 8 to about 200.

DETAILED DESCRIPTION OF THE INVENTION

Definitions

The terms "natural oils," "natural feedstocks," or "natural oil feedstocks" may refer to oils derived from plants or animal sources. The term "natural oil" includes natural oil derivatives, unless otherwise indicated. The terms also include modified plant or animal sources (e.g., genetically modified plant or animal sources), unless indicated otherwise. Examples of natural oils include, but are not limited to, vegetable oils, algae oils, fish oils, animal fats, tall oils, derivatives of these oils, combinations of any of these oils, and the like. Representative non-limiting examples of vegetable oils include canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, pennycress oil, camelina oil, and castor oil. Representative non-limiting examples of animal fats include lard, tallow, poultry fat, yellow grease, and fish oil. Tall oils are by-products of wood pulp manufacture.

The term "natural oil derivatives" refers to derivatives thereof derived from natural oil. The methods used to form these natural oil derivatives may include one or more of addition, neutralization, overbasing, saponification, transesterification, esterification, amidification, hydrogenation, isomerization, oxidation, alkylation, acylation, sulfurization, sulfonation, rearrangement, reduction, fermentation, pyrolysis, hydrolysis, liquefaction, anaerobic digestion, hydrothermal processing, gasification or a combination of two or more thereof. Examples of natural derivatives thereof may include carboxylic acids, gums, phospholipids, soapstock, acidulated soapstock, distillate or distillate sludge, fatty acids, fatty acid esters, as well as hydroxy substituted variations thereof, including unsaturated polyol esters. In some embodiments, the natural oil derivative may comprise an unsaturated carboxylic acid having from about 5 to about 30 carbon atoms, having one or more carbon-carbon double bonds in the hydrocarbon (alkene) chain. The natural oil derivative may also comprise an unsaturated fatty acid alkyl (e.g., methyl) ester derived from a glyceride of natural oil. For example, the natural oil derivative may be a fatty acid methyl ester ("FAME") derived from the glyceride of the natural oil. In some embodiments, a feedstock includes canola or soybean oil, as a non-limiting example, refined, bleached, and deodorized soybean oil (i.e., RBD soybean oil).

The term "free hydrocarbon" refers to any one or combination of unsaturated or saturated straight, branched, or cyclic hydrocarbons in the $C_2$ to $C_{22}$ range.

The term "metathesis monomer" refers to a single entity that is the product of a metathesis reaction which comprises a molecule of a compound with one or more carbon-carbon double bonds which has undergone an alkylidene unit interchange via one or more of the carbon-carbon double bonds either within the same molecule (intramolecular metathesis) and/or with a molecule of another compound containing one or more carbon-carbon double bonds such as an olefin (intermolecular metathesis).

The term "metathesis dimer" refers to the product of a metathesis reaction wherein two reactant compounds, which can be the same or different and each with one or more carbon-carbon double bonds, are bonded together via one or more of the carbon-carbon double bonds in each of the reactant compounds as a result of the metathesis reaction.

The term "metathesis trimer" refers to the product of one or more metathesis reactions wherein three molecules of two or more reactant compounds, which can be the same or different and each with one or more carbon-carbon double bonds, are bonded together via one or more of the carbon-carbon double bonds in each of the reactant compounds as a result of the one or more metathesis reactions, the trimer containing three bonded groups derived from the reactant compounds.

The term "metathesis tetramer" refers to the product of one or more metathesis reactions wherein four molecules of two or more reactant compounds, which can be the same or different and each with one or more carbon-carbon double bonds, are bonded together via one or more of the carbon-carbon double bonds in each of the reactant compounds as a result of the one or more metathesis reactions, the tetramer containing four bonded groups derived from the reactant compounds.

The term "metathesis pentamer" refers to the product of one or more metathesis reactions wherein five molecules of two or more reactant compounds, which can be the same or different and each with one or more carbon-carbon double bonds, are bonded together via one or more of the carbon-carbon double bonds in each of the reactant compounds as a result of the one or more metathesis reactions, the pentamer containing five bonded groups derived from the reactant compounds.

The term "metathesis hexamer" refers to the product of one or more metathesis reactions wherein six molecules of two or more reactant compounds, which can be the same or different and each with one or more carbon-carbon double bonds, are bonded together via one or more of the carbon-carbon double bonds in each of the reactant compounds as a result of the one or more metathesis reactions, the hexamer containing six bonded groups derived from the reactant compounds.

The term "metathesis heptamer" refers to the product of one or more metathesis reactions wherein seven molecules of two or more reactant compounds, which can be the same or different and each with one or more carbon-carbon double bonds, are bonded together via one or more of the carbon-carbon double bonds in each of the reactant compounds as a result of the one or more metathesis reactions, the heptamer containing seven bonded groups derived from the reactant compounds.

The term "metathesis octamer" refers to the product of one or more metathesis reactions wherein eight molecules of two or more reactant compounds, which can be the same or different and each with one or more carbon-carbon double bonds, are bonded together via one or more of the carbon-carbon double bonds in each of the reactant compounds as a result of the one or more metathesis reactions, the octamer containing eight bonded groups derived from the reactant compounds.

The term "metathesis nonamer" refers to the product of one or more metathesis reactions wherein nine molecules of two or more reactant compounds, which can be the same or different and each with one or more carbon-carbon double bonds, are bonded together via one or more of the carbon-carbon double bonds in each of the reactant compounds as a result of the one or more metathesis reactions, the nonamer containing nine bonded groups derived from the reactant compounds.

The term "metathesis decamer" refers to the product of one or more metathesis reactions wherein ten molecules of two or more reactant compounds, which can be the same or different and each with one or more carbon-carbon double bonds, are bonded together via one or more of the carbon-carbon double bonds in each of the reactant compounds as a result of the one or more metathesis reactions, the decamer containing ten bonded groups derived from the reactant compounds.

The term "metathesis oligomer" refers to the product of one or more metathesis reactions wherein two or more molecules (e.g., 2 to about 10, or 2 to about 4) of two or more reactant compounds, which can be the same or different and each with one or more carbon-carbon double bonds, are bonded together via one or more of the carbon-carbon double bonds in each of the reactant compounds as a result of the one or more metathesis reactions, the oligomer containing a few (e.g., 2 to about 10, or 2 to about 4) bonded groups derived from the reactant compounds. In some embodiments, the term "metathesis oligomer" may include metathesis reactions wherein greater than ten molecules of two or more reactant compounds, which can be the same or different and each with one or more carbon-carbon double bonds, are bonded together via one or more of the carbon-carbon double bonds in each of the reactant compounds as a result of the one or more metathesis reactions, the oligomer containing greater than ten bonded groups derived from the reactant compounds.

As used herein, the terms "metathesize" and "metathesizing" may refer to the reacting of a unsaturated polyol ester feedstock in the presence of a metathesis catalyst to form a metathesized unsaturated polyol ester product comprising a new olefinic compound and/or esters. Metathesizing may refer to cross-metathesis (a.k.a. co-metathesis), self-metathesis, ring-opening metathesis, ring-opening metathesis polymerizations ("ROMP"), ring-closing metathesis ("RCM"), and acyclic diene metathesis ("ADMET"). As a non-limiting example, metathesizing may refer to reacting two triglycerides present in a natural feedstock (self-metathesis) in the presence of a metathesis catalyst, wherein each triglyceride has an unsaturated carbon-carbon double bond, thereby forming an oligomer having a new mixture of olefins and esters that may comprise one or more of: metathesis monomers, metathesis dimers, metathesis trimers, metathesis tetramers, metathesis pentamers, and higher order metathesis oligomers (e.g., metathesis hexamers, metathesis, metathesis heptamers, metathesis octamers, metathesis nonamers, metathesis decamers, and higher than metathesis decamers and above).

As used herein, the term "polyol" means an organic material comprising at least two hydroxy moieties.

As used herein, the articles including "a" and "an" when used in a claim, are understood to mean one or more of what is claimed or described.

As used herein, the terms "include", "includes" and "including" are meant to be non-limiting. Unless otherwise noted, all component or composition levels are in reference to the active portion of that component or composition, and are exclusive of impurities, for example, residual solvents or by-products, which may be present in commercially available sources of such components or compositions.

All percentages and ratios are calculated by weight unless otherwise indicated. All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Compositions, Articles and Methods of Use

TABLE 1

Compositions

| Comp. No. | Composition |
|---|---|
| 1 | A composition comprising,<br>a) a metathesized unsaturated polyol ester, said metathesized unsaturated polyol ester having one or more of the following properties:<br>(i) a weight average molecular weight of from about 5,000 Daltons to about 50,000 Daltons, from about 5,500 Daltons to about 50,000 Daltons, from about 5,500 Daltons to about 40,000 Daltons, or from about 6,000 Daltons to about 30,000 Daltons;<br>(ii) an oligomer index from greater than 0 to 1, from 0.001 to 1, 0.01 to 1, or from 0.05 to 1;<br>(iii) an iodine value of from about 30 to about 200, from about 30 to about 150, from about 30 to about 120, or from about 50 to about 110. |
| 2 | In one aspect of said composition 1 of Table 1, said metathesized unsaturated polyol ester has the weight average molecular weight property from a)(i) above. |
| 3 | In one aspect of said composition 1 of Table 1, said metathesized unsaturated polyol ester has the oligomer index property from a)(ii) above. |
| 4 | In one aspect of said composition 1 of Table 1, said metathesized unsaturated polyol ester has the iodine value property from a)(iii) above. |
| 5 | In one aspect of said composition 1 of Table 1, said metathesized unsaturated polyol ester has the property from a)(i) and from a)(ii) above. |
| 6 | In one aspect of said composition 1 of Table 1, said metathesized unsaturated polyol ester has the properties from a)(i) and from a)(iii) above. |
| 7 | In one aspect of said composition 1 of Table 1, said metathesized unsaturated polyol ester has the properties from a)(ii) and from a)(iii) above. |
| 8 | In one aspect of said composition 1 of Table 1, said metathesized unsaturated polyol ester has the properties from a)(i), a)(ii) and a)(iii) above. |
| 9 | In one aspect, of compositions 1, 2, 3, 4, 5, 6, 7, and 8 of Table 1, said metathesized unsaturated polyol ester has a free hydrocarbon content, based on total weight of metathesized unsaturated polyol ester, of from about 0% to about 5%, from about 0.1% to about 5%, from about 0.1% to about 4%, or from about 0.1 to about 3%. |

TABLE 1-continued

Compositions

| Comp. No. | Composition |
|---|---|
| 10 | In one aspect of Table 1 Compositions 1, 2, 3, 4, 5, 6, 7, 8, and 9 the metathesized unsaturated polyol ester is metathesized at least once. |
| 11 | In one aspect, of compositions 1, 2, 3, 4, 5, 6, 7, 8, 9 and 10 of Table 1, said composition comprises, based on total composition weight, from about 0.1% to about 50%, from about 0.5% to about 30%, or from about 1% to about 20% of said metathesized unsaturated polyol ester. |

TABLE 2

Compositions

| Comp. No. | Composition |
|---|---|
| 1 | A composition comprising:<br>a) a metathesized unsaturated polyol ester, said metathesized unsaturated polyol ester having a weight average molecular weight of from about 2,000 Daltons to about 50,000 Daltons, from about 2,500 Daltons to about 50,000 Daltons, from about 3,000 Daltons to about 40,000 Daltons, from about 3,000 Daltons to about 30,000 Daltons; and one or more of the following properties:<br>(i) a free hydrocarbon content, based on total weight of metathesized unsaturated polyol ester, of from about 0% to about 5%, from about 0.1% to about 5%, from about 0.1% to about 4%, or from about 0.1 to about 3%;<br>(ii) an oligomer index from greater than 0 to 1, from 0.001 to 1, 0.01 to 1, or from 0.05 to 1;<br>(iii) an iodine value of from about 8 to about 200, from about 10 to about 200, from about 20 to about 150, from about 30 to about 120. |
| 2 | In one aspect of said composition 1 of Table 2, said metathesized unsaturated polyol ester has the free hydrocarbon content property from a)(i) above. |
| 3 | In one aspect of said composition 1 of Table 2, said metathesized unsaturated polyol ester has the oligomer index property from a)(ii) above. |
| 4 | In one aspect of said composition 1 of Table 2, said metathesized unsaturated polyol ester has the iodine value property from a)(iii) above. |
| 5 | In one aspect of said composition 1 of Table 2, said metathesized unsaturated polyol ester has the property from a)(i) and from a)(ii) above. |
| 6 | In one aspect of said composition 1 of Table 2, said metathesized unsaturated polyol ester has the properties from a)(i) and from a)(iii) above. |
| 7 | In one aspect of said composition 1 of Table 2, said metathesized unsaturated polyol ester has the properties from a)(ii) and from a)(iii) above. |
| 8 | In one aspect of said composition 1 of Table 2, said metathesized unsaturated polyol ester has the properties from a)(i), a)(ii) and from a)(iii) above. |
| 9 | In one aspect of Table 2 Compositions 1, 2, 3, 4, 5, 6, 7, and 8 the metathesized unsaturated polyol ester is metathesized at least once. |
| 10 | In one aspect, of compositions 1, 2, 3, 4, 5, 6, 7, and 9 of Table 2, said composition comprises, based on total composition weight, from about 0.1% to about 50%, from about 0.5% to about 30% or from about 1% to about 20% of said metathesized unsaturated polyol ester. |

In one aspect, Table 1 Compositions 1, 2, 3, 4, 5, 6, 7, 8, 9, 10 and 11; and Table 2 Compositions 1, 2, 3, 4, 5, 6, 7, 8, 9 and 10 the metathesized unsaturated polyol ester is derived from a natural polyol ester and/or a synthetic polyol ester, in one aspect, said natural polyol ester is selected from the group consisting of a vegetable oil, an animal fat, an algae oil and mixtures thereof; and said synthetic polyol ester is derived from a material selected from the group consisting of ethylene glycol, propylene glycol, glycerol, polyglycerol, polyethylene glycol, polypropylene glycol, poly(tetramethylene ether) glycol, pentaerythritol, dipentaerythritol, tripentaerythritol, trimethylolpropane, neopentyl glycol, a sugar, in one aspect, sucrose, and mixtures thereof.

In one aspect, Table 1 Compositions 1, 2, 3, 4, 5, 6, 7, 8, 9, 10 and 11; and Table 2 Compositions 1, 2, 3, 4, 5, 6, 7, 8, 9 and 10 the metathesized unsaturated polyol ester is selected from the group consisting of metathesized Abyssinian oil, metathesized Almond Oil, metathesized Apricot Oil, metathesized Apricot Kernel oil, metathesized Argan oil, metathesized Avocado Oil, metathesized Babassu Oil, metathesized Baobab Oil, metathesized Black Cumin Oil, metathesized Black Currant Oil, metathesized Borage Oil, metathesized Camelina oil, metathesized *Carinata* oil, metathesized Canola oil, metathesized Castor oil, metathesized Cherry Kernel Oil, metathesized Coconut oil, metathesized Corn oil, metathesized Cottonseed oil, metathesized Echium Oil, metathesized Evening Primrose Oil, metathesized Flax Seed Oil, metathesized Grape Seed Oil, metathesized Grapefruit Seed Oil, metathesized Hazelnut Oil, metathesized Hemp Seed Oil, metathesized Jatropha oil, metathesized Jojoba Oil, metathesized Kukui Nut Oil, metathesized Linseed Oil, metathesized Macadamia Nut Oil, metathesized Meadowfoam Seed Oil, metathesized Moringa Oil, metathesized Neem Oil, metathesized Olive Oil, metathesized Palm Oil, metathesized Palm Kernel Oil, metathesized Peach Kernel Oil, metathesized Peanut Oil, metathesized Pecan Oil, metathesized Pennycress oil, metathesized *Perilla* Seed Oil, metathesized Pistachio Oil, metathesized Pomegranate Seed Oil, metathesized Pongamia oil, metathesized Pumpkin Seed Oil, metathesized Raspberry Oil, metathesized Red Palm Olein, metathesized Rice Bran Oil, metathesized Rosehip Oil, metathesized Safflower Oil, metathesized Seabuckthorn Fruit Oil, metathesized Sesame Seed Oil, metathesized Shea Olein, metathesized Sunflower Oil, metathesized Soybean Oil, metathesized Tonka Bean Oil, metathesized Tung Oil, metathesized Walnut Oil, metathesized Wheat Germ Oil, metathesized High Oleoyl Soybean Oil, metathesized High Oleoyl Sunflower Oil, metathesized High Oleoyl Safflower Oil, metathesized High Erucic Acid Rapeseed Oil, and mixtures thereof.

Methods of Making Compositions

The compositions of the present invention can be formulated into any suitable form and prepared by any process chosen by the formulator, non-limiting examples of which are described in U.S. Pat. No. 5,879,584 which is incorporated herein by reference. For example, the metathesized unsaturated polyol esters can be combined directly with the composition's other ingredients without pre-emulsification and/or pre-mixing to form the finished products. Alternatively, the metathesized unsaturated polyol esters can be combined with surfactants or emulsifiers, solvents, suitable adjuncts, and/or any other suitable ingredients to prepare emulsions prior to compounding the finished products.

Suitable equipment for use in the processes disclosed herein may include continuous stirred tank reactors, homogenizers, turbine agitators, recirculating pumps, paddle mixers, plough shear mixers, ribbon blenders, vertical axis granulators and drum mixers, both in batch and, where available, in continuous process configurations, spray dryers, and extruders. Such equipment can be obtained from Lodige GmbH (Paderborn, Germany), Littleford Day, Inc. (Florence, Ky., U.S.A.), Forberg AS (Larvik, Norway), Glatt Ingenieurtechnik GmbH (Weimar, Germany), Niro (Soeborg, Denmark), Hosokawa Bepex Corp. (Minneapolis, Minn., U.S.A.), Arde Barinco (New Jersey, U.S.A.).

Metathesized Unsaturated Polyol Ester

Exemplary metathesized unsaturated polyol esters and their starting materials are set forth in U.S. Patent Applications U.S. 2009/0220443 A1, U.S. 2013/0344012 A1 and US 2014/0357714 A1, which are incorporated herein by reference. A metathesized unsaturated polyol ester refers to the product obtained when one or more unsaturated polyol ester ingredient(s) are subjected to a metathesis reaction. Metathesis is a catalytic reaction that involves the interchange of alkylidene units among compounds containing one or more double bonds (i.e., olefinic compounds) via the formation and cleavage of the carbon-carbon double bonds. Metathesis may occur between two of the same molecules (often referred to as self-metathesis) and/or it may occur between two different molecules (often referred to as cross-metathesis). Self-metathesis may be represented schematically as shown in Equation I.

(I)

where $R^1$ and $R^2$ are organic groups.

Cross-metathesis may be represented schematically as shown in Equation II

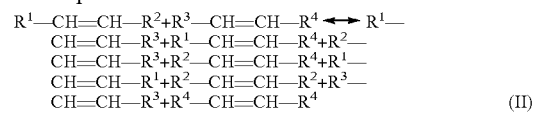
(II)

where $R^1$, $R^2$, $R^3$, and $R^4$ are organic groups.

When a polyol ester comprises molecules having more than one carbon-carbon double bond, self-metathesis may result in oligomerization or polymerization of the unsaturates in the starting material. For example, Equation C depicts metathesis oligomerization of a representative species (e.g., a polyol ester) having more than one carbon-carbon double bond. In Equation C, the self-metathesis reaction results in the formation of metathesis dimers, metathesis trimers, and metathesis tetramers. Although not shown, higher order oligomers such as metathesis pentamers, hexamers, heptamers, octamers, nonamers, decamers, and higher than decamers, and mixtures of two or more thereof, may also be formed. The number of metathesis repeating units or groups in the metathesized natural oil may range from 1 to about 100, or from 2 to about 50, or from 2 to about 30, or from 2 to about 10, or from 2 to about 4. The molecular weight of the metathesis dimer may be greater than the molecular weight of the unsaturated polyol ester from which the dimer is formed. Each of the bonded polyol ester molecules may be referred to as a "repeating unit or group." Typically, a metathesis trimer may be formed by the cross-metathesis of a metathesis dimer with an unsaturated polyol ester. Typically, a metathesis tetramer may be formed by the cross-metathesis of a metathesis trimer with an unsaturated polyol ester or formed by the cross-metathesis of two metathesis dimers.

Equation C

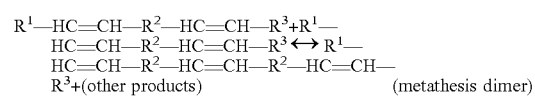
(metathesis dimer)

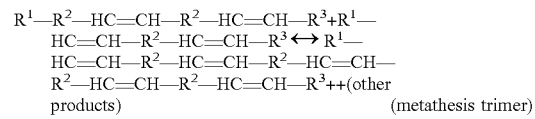
(metathesis trimer)

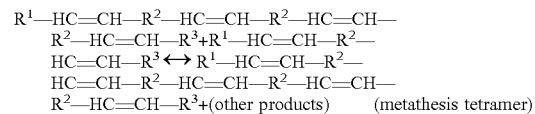
(metathesis tetramer)

where $R^1$, $R^2$, and $R^3$ are organic groups.

As a starting material, metathesized unsaturated polyol esters are prepared from one or more unsaturated polyol esters. As used herein, the term "unsaturated polyol ester" refers to a compound having two or more hydroxyl groups wherein at least one of the hydroxyl groups is in the form of an ester and wherein the ester has an organic group including at least one carbon-carbon double bond. In many embodiments, the unsaturated polyol ester can be represented by the general structure (I):

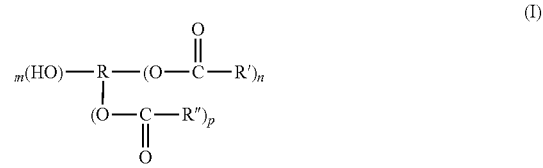
(I)

where n≥1;
m≥0;
p≥0;
(n+m+p)≥2;
R is an organic group;
R' is an organic group having at least one carbon-carbon double bond; and
R" is a saturated organic group.

In many embodiments of the invention, the unsaturated polyol ester is an unsaturated polyol ester of glycerol. Unsaturated polyol esters of glycerol have the general structure (II):

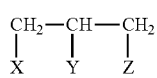

where —X, —Y, and —Z are independently selected from the group consisting of:
—OH; —(O—C(=O)—R'); and —(O—C(=O)—R");
where —R' is an organic group having at least one carbon-carbon double bond and —R" is a saturated organic group.

In structure (II), at least one of —X, —Y, and —Z is —(O—C(=O)—R').

In some embodiments, R' is a straight or branched chain hydrocarbon having about 50 or less carbon atoms (e.g., about 36 or less carbon atoms or about 26 or less carbon atoms) and at least one carbon-carbon double bond in its chain. In some embodiments, R' is a straight or branched chain hydrocarbon having about 6 carbon atoms or greater (e.g., about 10 carbon atoms or greater or about 12 carbon atoms or greater) and at least one carbon-carbon double bond in its chain. In some embodiments, R' may have two or more carbon-carbon double bonds in its chain. In other embodiments, R' may have three or more double bonds in its chain. In exemplary embodiments, R' has 17 carbon atoms and 1 to 3 carbon-carbon double bonds in its chain. Representative examples of R' include:

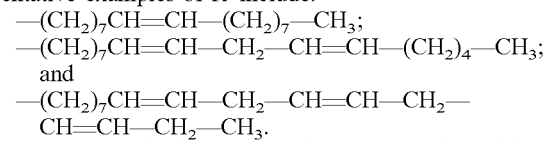

In some embodiments, R" is a saturated straight or branched chain hydrocarbon having about 50 or less carbon atoms (e.g., about 36 or less carbon atoms or about 26 or less carbon atoms). In some embodiments, R" is a saturated straight or branched chain hydrocarbon having about 6 carbon atoms or greater (e.g., about 10 carbon atoms or greater or about 12 carbon atoms or greater. In exemplary embodiments, R" has 15 carbon atoms or 17 carbon atoms.

Sources of unsaturated polyol esters of glycerol include synthesized oils, natural oils (e.g., vegetable oils, algae oils, bacterial derived oils, and animal fats), combinations of these, and the like. Recycled used vegetable oils may also be used. Representative non-limiting examples of vegetable oils include Abyssinian oil, Almond Oil, Apricot Oil, Apricot Kernel oil, Argan oil, Avocado Oil, Babassu Oil, Baobab Oil, Black Cumin Oil, Black Currant Oil, Borage Oil, Camelina oil, *Carinata* oil, Canola oil, Castor oil, Cherry Kernel Oil, Coconut oil, Corn oil, Cottonseed oil, Echium Oil, Evening Primrose Oil, Flax Seed Oil, Grape Seed Oil, Grapefruit Seed Oil, Hazelnut Oil, Hemp Seed Oil, Jatropha oil, Jojoba Oil, Kukui Nut Oil, Linseed Oil, Macadamia Nut Oil, Meadowfoam Seed Oil, Moringa Oil, Neem Oil, Olive Oil, Palm Oil, Palm Kernel Oil, Peach Kernel Oil, Peanut Oil, Pecan Oil, Pennycress oil, *Perilla* Seed Oil, Pistachio Oil, Pomegranate Seed Oil, Pongamia oil, Pumpkin Seed Oil, Raspberry Oil, Red Palm Olein, Rice Bran Oil, Rosehip Oil, Safflower Oil, Seabuckthorn Fruit Oil, Sesame Seed Oil, Shea Olein, Sunflower Oil, Soybean Oil, Tonka Bean Oil, Tung Oil, Walnut Oil, Wheat Germ Oil, High Oleoyl Soybean Oil, High Oleoyl Sunflower Oil, High Oleoyl Safflower Oil, High Erucic Acid Rapeseed Oil, combinations of these, and the like. Representative non-limiting examples of animal fats include lard, tallow, chicken fat, yellow grease, fish oil, emu oil, combinations of these, and the like. A representative non-limiting example of a synthesized oil includes tall oil, which is a byproduct of wood pulp manufacture. In some embodiments, the natural oil is refined, bleached, and/or deodorized.

Other examples of unsaturated polyol esters include esters such as those derived from ethylene glycol or propylene glycol, polyethylene glycol, polypropylene glycol, or poly(tetramethylene ether) glycol, esters such as those derived from pentaerythritol, dipentaerythritol, tripentaerythritol trimethylolpropane, or neopentyl glycol, or sugar esters such as SEFOSE®. Sugar esters such as SEFOSE® include one or more types of sucrose polyesters, with up to eight ester groups that could undergo a metathesis exchange reaction. Sucrose polyesters are derived from a natural resource and therefore, the use of sucrose polyesters can result in a positive environmental impact. Sucrose polyesters are polyester materials, having multiple substitution positions around the sucrose backbone coupled with the chain length, saturation, and derivation variables of the fatty chains. Such sucrose polyesters can have an esterification ("IBAR") of greater than about 5. In one embodiment the sucrose polyester may have an IBAR of from about 5 to about 8. In another embodiment the sucrose polyester has an IBAR of about 5-7, and in another embodiment the sucrose polyester has an IBAR of about 6. In yet another embodiment the sucrose polyester has an IBAR of about 8. As sucrose polyesters are derived from a natural resource, a distribution in the IBAR and chain length may exist. For example a sucrose polyester having an IBAR of 6, may contain a mixture of mostly IBAR of about 6, with some IBAR of about 5 and some IBAR of about 7. Additionally, such sucrose polyesters may have a saturation or iodine value ("IV") of about 3 to about 140. In another embodiment the sucrose polyester may have an IV of about 10 to about 120. In yet another embodiment the sucrose polyester may have an IV of about 20 to 100. Further, such sucrose polyesters have a chain length of about $C_{12}$ to $C_{20}$ but are not limited to these chain lengths.

Non-limiting examples of sucrose polyesters suitable for use include SEFOSE® 1618S, SEFOSE® 1618U, SEFOSE® 1618H, Sefa Soyate IMF 40, Sefa Soyate LP426, SEFOSE® 2275, SEFOSE® C1695, SEFOSE® C18:0 95, SEFOSE® C1495, SEFOSE® 1618H B6, SEFOSE® 1618S B6, SEFOSE® 1618U B6, Sefa Cottonate, SEFOSE® C1295, Sefa C895, Sefa C1095, SEFOSE® 1618S B4.5, all available from The Procter and Gamble Co. of Cincinnati, Ohio.

Other examples of suitable polyol esters may include but not be limited to sorbitol esters, maltitol esters, sorbitan esters, maltodextrin derived esters, xylitol esters, polyglycerol esters, and other sugar derived esters.

Natural oils of the type described herein typically are composed of triglycerides of fatty acids. These fatty acids may be either saturated, monounsaturated or polyunsaturated and contain varying chain lengths ranging from $C_8$ to $C_{30}$. The most common fatty acids include saturated fatty acids such as lauric acid (dodecanoic acid), myristic acid (tetradecanoic acid), palmitic acid (hexadecanoic acid), stearic acid (octadecanoic acid), arachidic acid (eicosanoic acid), and lignoceric acid (tetracosanoic acid); unsaturated acids include such fatty acids as palmitoleic (a $C_{16}$ acid), and oleic acid (a $C_{18}$ acid); polyunsaturated acids include such fatty acids as linoleic acid (a di-unsaturated $C_{18}$ acid), linolenic acid (a tri-unsaturated $C_{18}$ acid), and arachidonic acid (a tetra-unsubstituted $C_{20}$ acid). The natural oils are further comprised of esters of these fatty acids in random placement onto the three sites of the trifunctional glycerine molecule. Different natural oils will have different ratios of these fatty acids, and within a given natural oil there is a range of these acids as well depending on such factors as where a vegetable or crop is grown, maturity of the vegetable or crop, the weather during the growing season, etc. Thus, it is difficult to have a specific or unique structure for any given natural oil, but rather a structure is typically based on some statistical average. For example soybean oil contains a mixture of stearic acid, oleic acid, linoleic acid, and linolenic acid in the ratio of 15:24:50:11, and an average number of double bonds of 4.4-4.7 per triglyceride. One method of quantifying the number of double bonds is the iodine value (IV) which is defined as the number of grams of iodine that will react with 100 grams of oil. Therefore for soybean oil, the average iodine value range is from 120-140. Soybean oil may comprise about 95% by weight or greater (e.g., 99% weight or greater) triglycerides of fatty acids. Major fatty acids in the polyol esters of soybean oil include saturated fatty acids, as a non-limiting example, palmitic acid (hexadecanoic acid) and stearic acid (octadecanoic acid), and unsaturated fatty acids, as a non-limiting example, oleic acid (9-octadecenoic acid), linoleic acid (9,12octadecadienoic acid), and linolenic acid (9,12,15-octadecatrienoic acid).

In an exemplary embodiment, the vegetable oil is canola oil, for example, refined, bleached, and deodorized canola oil (i.e., RBD canola oil). Canola oil is an unsaturated polyol ester of glycerol that typically comprises about 95% weight or greater (e.g., 99% weight or greater) triglycerides of fatty acids. Major fatty acids in the polyol esters of canola oil include saturated fatty acids, for example, palmitic acid (hexadecanoic acid) and stearic acid (octadecanoic acid), and unsaturated fatty acids, for example, oleic acid (9-octadecenoic acid), linoleic acid (9,12-octadecadienoic acid), and linolenic acid (9,12,15-octadecatrienoic acid). Canola oil is a highly unsaturated vegetable oil with many of the triglyceride molecules having at least two unsaturated fatty acids (i.e., a polyunsaturated triglyceride).

In exemplary embodiments, an unsaturated polyol ester is self-metathesized in the presence of a metathesis catalyst to form a metathesized composition. Typically, after metathesis has occurred, the metathesis catalyst is removed from the resulting product. One method of removing the catalyst is treatment of the metathesized product with clay. In many embodiments, the metathesized composition comprises one or more of: metathesis monomers, metathesis dimers, metathesis trimers, metathesis tetramers, metathesis pentamers, and higher order metathesis oligomers (e.g., metathesis hexamers). A metathesis dimer refers to a compound formed when two unsaturated polyol ester molecules are covalently bonded to one another by a self-metathesis reaction. In many embodiments, the molecular weight of the metathesis dimer is greater than the molecular weight of the individual unsaturated polyol ester molecules from which the dimer is formed. A metathesis trimer refers to a compound formed when three unsaturated polyol ester molecules are covalently bonded together by metathesis reactions. In many embodiments, a metathesis trimer is formed by the cross-metathesis of a metathesis dimer with an unsaturated polyol ester. A metathesis tetramer refers to a compound formed when four unsaturated polyol ester molecules are covalently bonded together by metathesis reactions. In many embodiments, a metathesis tetramer is formed by the cross-metathesis of a metathesis trimer with an unsaturated polyol ester. Metathesis tetramers may also be formed, for example, by the cross-metathesis of two metathesis dimers. Higher order metathesis products may also be formed. For example, metathesis pentamers and metathesis hexamers may also be formed. The self-metathesis reaction also results in the formation of internal olefin compounds that may be linear or cyclic. If the metathesized polyol ester is fully or partially hydrogenated, the linear and cyclic olefins would typically be fully or partially converted to the corresponding saturated linear and cyclic hydrocarbons. The linear/cyclic olefins and saturated linear/cyclic hydrocarbons may remain in the metathesized polyol ester or they may be removed or partially removed from the metathesized polyol ester using one or more known stripping techniques, including but not limited to wipe film evaporation, falling film evaporation, rotary evaporation, steam stripping, vacuum distillation, etc.

In some embodiments, the unsaturated polyol ester is partially hydrogenated before being metathesized. For example, in some embodiments, the unsaturated polyol ester is partially hydrogenated to achieve an iodine value (IV) of about 120 or less before subjecting the partially hydrogenated polyol ester to metathesis.

In some embodiments, the unsaturated polyol ester may be hydrogenated (e.g., fully or partially hydrogenated) in order to improve the stability of the oil or to modify its viscosity or other properties. Representative techniques for hydrogenating unsaturated polyol esters are known in the art and are discussed herein.

In some embodiments, the natural oil is winterized. Winterization refers to the process of: (1) removing waxes and other non-triglyceride constituents, (2) removing naturally occurring high-melting triglycerides, and (3) removing high-melting triglycerides formed during partial hydrogenation. Winterization may be accomplished by known methods including, for example, cooling the oil at a controlled rate in order to cause crystallization of the higher melting components that are to be removed from the oil. The crystallized high melting components are then removed from the oil by filtration resulting in winterized oil. Winterized soybean oil is commercially available from Cargill, Incorporated (Minneapolis, Minn.).

Method of Making Metathesized Unsaturated Polyol Ester

The self-metathesis of unsaturated polyol esters is typically conducted in the presence of a catalytically effective amount of a metathesis catalyst. The term "metathesis catalyst" includes any catalyst or catalyst system that catalyzes a metathesis reaction. Any known or future-developed metathesis catalyst may be used, alone or in combination with one or more additional catalysts. Suitable homogeneous metathesis catalysts include combinations of a transition metal halide or oxo-halide (e.g., $WOCl_4$ or $WCl_6$) with an alkylating cocatalyst (e.g., $Me_4Sn$), or alkylidene (or carbene) complexes of transition metals, particularly Ru or W. These include first and second-generation Grubbs catalysts, Grubbs-Hoveyda catalysts, and the like. Suitable alkylidene catalysts have the

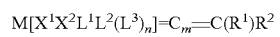

general structure:

where M is a Group 8 transition metal, $L^1$, $L^2$, and $L^3$ are neutral electron donor ligands, n is 0 (such that $L^3$ may not be present) or 1, m is 0, 1, or 2, $X^1$ and $X^2$ are anionic ligands, and $R^1$ and $R^2$ are independently selected from H, hydrocarbyl, substituted hydrocarbyl, heteroatom-containing hydrocarbyl, substituted heteroatom-containing hydrocarbyl, and functional groups. Any two or more of $X^1$, $X^2$, $L^1$, $L^2$, $L^3$, $R^1$ and $R^2$ can form a cyclic group and any one of those groups can be attached to a support.

First-generation Grubbs catalysts fall into this category where m=n=0 and particular selections are made for n, $X^1$, $X^2$, $L^1$, $L^2$, $L^3$, $R^1$ and $R^2$ as described in U.S. Pat. Appl. Publ. No. 2010/0145086, the teachings of which related to all metathesis catalysts are incorporated herein by reference.

Second-generation Grubbs catalysts also have the general formula described above, but $L^1$ is a carbene ligand where the carbene carbon is flanked by N, O, S, or P atoms, preferably by two N atoms. Usually, the carbene ligand is part of a cyclic group. Examples of suitable second-generation Grubbs catalysts also appear in the '086 publication.

In another class of suitable alkylidene catalysts, $L^1$ is a strongly coordinating neutral electron donor as in first- and second-generation Grubbs catalysts, and $L^2$ and $L^3$ are weakly coordinating neutral electron donor ligands in the form of optionally substituted heterocyclic groups. Thus, $L^2$ and $L^3$ are pyridine, pyrimidine, pyrrole, quinoline, thiophene, or the like.

In yet another class of suitable alkylidene catalysts, a pair of substituents is used to form a bi- or tridentate ligand, such as a biphosphine, dialkoxide, or alkyldiketonate. Grubbs-Hoveyda catalysts are a subset of this type of catalyst in which $L^2$ and $R^2$ are linked. Typically, a neutral oxygen or nitrogen coordinates to the metal while also being bonded to a carbon that is α-, β-, or γ- with respect to the carbene carbon to provide the bidentate ligand. Examples of suitable Grubbs-Hoveyda catalysts appear in the '086 publication.

The structures below provide just a few illustrations of suitable catalysts that may be used:

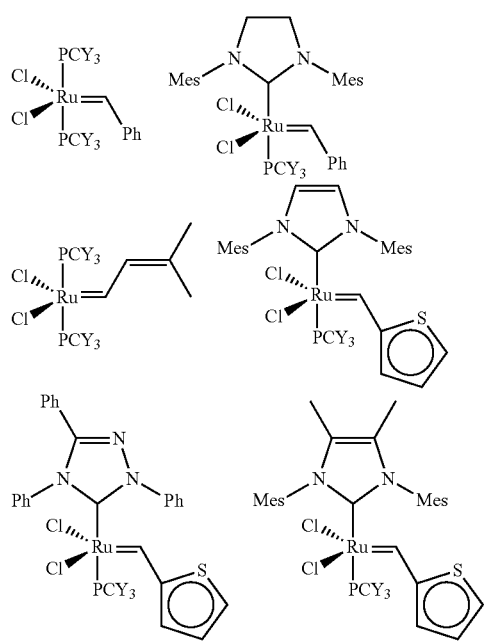

An immobilized catalyst can be used for the metathesis process. An immobilized catalyst is a system comprising a catalyst and a support, the catalyst associated with the support. Exemplary associations between the catalyst and the support may occur by way of chemical bonds or weak interactions (e.g. hydrogen bonds, donor acceptor interactions) between the catalyst, or any portions thereof, and the support or any portions thereof. Support is intended to include any material suitable to support the catalyst. Typically, immobilized catalysts are solid phase catalysts that act on liquid or gas phase reactants and products. Exemplary supports are polymers, silica or alumina. Such an immobilized catalyst may be used in a flow process. An immobilized catalyst can simplify purification of products and recovery of the catalyst so that recycling the catalyst may be more convenient.

In certain embodiments, prior to the metathesis reaction, the unsaturated polyol ester feedstock may be treated to render the natural oil more suitable for the subsequent metathesis reaction. In one embodiment, the treatment of the unsaturated polyol ester involves the removal of catalyst poisons, such as peroxides, which may potentially diminish the activity of the metathesis catalyst. Non-limiting examples of unsaturated polyol ester feedstock treatment methods to diminish catalyst poisons include those described in PCT/US2008/09604, PCT/US2008/09635, and U.S. patent application Ser. Nos. 12/672,651 and 12/672,652, herein incorporated by reference in their entireties. In certain embodiments, the unsaturated polyol ester feedstock is thermally treated by heating the feedstock to a temperature greater than 100° C. in the absence of oxygen and held at the temperature for a time sufficient to diminish catalyst poisons in the feedstock. In other embodiments, the temperature is between approximately 100° C. and 300° C., between approximately 120° C. and 250° C., between approximately 150° C. and 210° C., or approximately between 190 and 200° C. In one embodiment, the absence of oxygen is achieved by sparging the unsaturated polyol ester feedstock with nitrogen, wherein the nitrogen gas is pumped into the feedstock treatment vessel at a pressure of approximately 10 atm (150 psig).

In certain embodiments, the unsaturated polyol ester feedstock is chemically treated under conditions sufficient to diminish the catalyst poisons in the feedstock through a chemical reaction of the catalyst poisons. In certain embodiments, the feedstock is treated with a reducing agent or a cation-inorganic base composition. Non-limiting examples of reducing agents include bisulfate, borohydride, phosphine, thiosulfate, and combinations thereof.

In certain embodiments, the unsaturated polyol ester feedstock is treated with an adsorbent to remove catalyst poisons. In one embodiment, the feedstock is treated with a combination of thermal and adsorbent methods. In another embodiment, the feedstock is treated with a combination of chemical and adsorbent methods. In another embodiment, the treatment involves a partial hydrogenation treatment to modify the unsaturated polyol ester feedstock's reactivity with the metathesis catalyst. Additional non-limiting examples of feedstock treatment are also described below when discussing the various metathesis catalysts.

In certain embodiments, a ligand may be added to the metathesis reaction mixture. In many embodiments using a ligand, the ligand is selected to be a molecule that stabilizes the catalyst, and may thus provide an increased turnover number for the catalyst. In some cases the ligand can alter reaction selectivity and product distribution. Examples of ligands that can be used include Lewis base ligands, such as, without limitation, trialkylphosphines, for example tricyclohexylphosphine and tributyl phosphine; triarylphosphines, such as triphenylphosphine; diarylalkylphosphines, such as, diphenylcyclohexylphosphine; pyridines, such as 2,6-dimethylpyridine, 2,4,6-trimethylpyridine; as well as other Lewis basic ligands, such as phosphine oxides and phosphinites. Additives may also be present during metathesis that increase catalyst lifetime.

Any useful amount of the selected metathesis catalyst can be used in the process. For example, the molar ratio of the unsaturated polyol ester to catalyst may range from about 5:1 to about 10,000,000:1 or from about 50:1 to 500,000:1. In some embodiments, an amount of about 1 to about 10 ppm, or about 2 ppm to about 5 ppm, of the metathesis catalyst per double bond of the starting composition (i.e., on a mole/mole basis) is used.

In some embodiments, the metathesis reaction is catalyzed by a system containing both a transition and a non-transition metal component. The most active and largest number of catalyst systems are derived from Group VI A transition metals, for example, tungsten and molybdenum.

Multiple, sequential metathesis reaction steps may be employed. For example, the metathesized unsaturated polyol ester product may be made by reacting an unsaturated polyol ester in the presence of a metathesis catalyst to form a first metathesized unsaturated polyol ester product. The first metathesized unsaturated polyol ester product may then be reacted in a self-metathesis reaction to form another metathesized unsaturated polyol ester product. Alternatively, the first metathesized unsaturated polyol ester product may be reacted in a cross-metathesis reaction with an unsaturated polyol ester to form another metathesized unsaturated polyol ester product. Also in the alternative, the transesterified products, the olefins and/or esters may be further metathesized in the presence of a metathesis catalyst. Such multiple and/or sequential metathesis reactions can be performed as many times as needed, and at least one or more times, depending on the processing/compositional requirements as understood by a person skilled in the art. As used herein, a "metathesized unsaturated polyol ester product" may include products that have been once metathesized and/or multiply metathesized. These procedures may be used to form metathesis dimers, metathesis trimers, metathesis tetramers, metathesis pentamers, and higher order metathesis oligomers (e.g., metathesis hexamers, metathesis heptamers, metathesis octamers, metathesis nonamers, metathesis decamers, and higher than metathesis decamers). These procedures can be repeated as many times as desired (for example, from 2 to about 50 times, or from 2 to about 30 times, or from 2 to about 10 times, or from 2 to about 5 times, or from 2 to about 4 times, or 2 or 3 times) to provide the desired metathesis oligomer or polymer which may comprise, for example, from 2 to about 100 bonded groups, or from 2 to about 50, or from 2 to about 30, or from 2 to about 10, or from 2 to about 8, or from 2 to about 6 bonded groups, or from 2 to about 4 bonded groups, or from 2 to about 3 bonded groups. In certain embodiments, it may be desirable to use the metathesized unsaturated polyol ester products produced by cross metathesis of an unsaturated polyol ester, or blend of unsaturated polyol esters, with a C2-C100 olefin, as the reactant in a self-metathesis reaction to produce another metathesized unsaturated polyol ester product. Alternatively, metathesized products produced by cross metathesis of an unsaturated polyol ester, or blend of unsaturated polyol esters, with a C2-C100 olefin can be combined with an unsaturated polyol ester, or blend of unsaturated polyol esters, and further metathesized to produce another metathesized unsaturated polyol ester product.

The metathesis process can be conducted under any conditions adequate to produce the desired metathesis products. For example, stoichiometry, atmosphere, solvent, temperature, and pressure can be selected by one skilled in the art to produce a desired product and to minimize undesirable byproducts. The metathesis process may be conducted under an inert atmosphere. Similarly, if a reagent is supplied as a gas, an inert gaseous diluent can be used. The inert atmosphere or inert gaseous diluent typically is an inert gas, meaning that the gas does not interact with the metathesis catalyst to substantially impede catalysis. For example, particular inert gases are selected from the group consisting of helium, neon, argon, nitrogen, individually or in combinations thereof.

In certain embodiments, the metathesis catalyst is dissolved in a solvent prior to conducting the metathesis reaction. In certain embodiments, the solvent chosen may be selected to be substantially inert with respect to the metathesis catalyst. For example, substantially inert solvents include, without limitation, aromatic hydrocarbons, such as benzene, toluene, xylenes, etc.; halogenated aromatic hydrocarbons, such as chlorobenzene and dichlorobenzene; aliphatic solvents, including pentane, hexane, heptane, cyclohexane, etc.; and chlorinated alkanes, such as dichloromethane, chloroform, dichloroethane, etc. In one particular embodiment, the solvent comprises toluene. The metathesis reaction temperature may be a rate-controlling variable where the temperature is selected to provide a desired product at an acceptable rate. In certain embodiments, the metathesis reaction temperature is greater than about −40° C., greater than about −20° C., greater than about 0° C., or greater than about 10° C. In certain embodiments, the metathesis reaction temperature is less than about 150° C., or less than about 120° C. In one embodiment, the metathesis reaction temperature is between about 10° C. and about 120° C.

The metathesis reaction can be run under any desired pressure. Typically, it will be desirable to maintain a total pressure that is high enough to keep the cross-metathesis reagent in solution. Therefore, as the molecular weight of the cross-metathesis reagent increases, the lower pressure range typically decreases since the boiling point of the cross-metathesis reagent increases. The total pressure may be selected to be greater than about 0.1 atm (10 kPa), in some embodiments greater than about 0.3 atm (30 kPa), or greater than about 1 atm (100 kPa). Typically, the reaction pressure is no more than about 70 atm (7000 kPa), in some embodiments no more than about 30 atm (3000 kPa). A non-limiting exemplary pressure range for the metathesis reaction is from about 1 atm (100 kPa) to about 30 atm (3000 kPa). In certain embodiments it may be desirable to run the metathesis reactions under an atmosphere of reduced pressure. Conditions of reduced pressure or vacuum may be used to remove olefins as they are generated in a metathesis reaction, thereby driving the metathesis equilibrium towards the formation of less volatile products. In the case of a self-metathesis of a natural oil, reduced pressure can be used to remove Cu or lighter olefins including, but not limited to, hexene, nonene, and dodecene, as well as byproducts including, but not limited to cyclohexa-diene and benzene as the metathesis reaction proceeds. The removal of these species can be used as a means to drive the reaction towards the formation of diester groups and cross linked triglycerides.

Hydrogenation:

In some embodiments, the unsaturated polyol ester is partially hydrogenated before it is subjected to the metathesis reaction. Partial hydrogenation of the unsaturated polyol ester reduces the number of double bonds that are available for in the subsequent metathesis reaction. In some embodiments, the unsaturated polyol ester is metathesized to form a metathesized unsaturated polyol ester, and the metathesized unsaturated polyol ester is then hydrogenated (e.g., partially or fully hydrogenated) to form a hydrogenated metathesized unsaturated polyol ester.

Hydrogenation may be conducted according to any known method for hydrogenating double bond-containing compounds such as vegetable oils. In some embodiments, the unsaturated polyol ester or metathesized unsaturated polyol ester is hydrogenated in the presence of a nickel catalyst that has been chemically reduced with hydrogen to an active state. Commercial examples of supported nickel hydrogenation catalysts include those available under the trade designations "NYSOFACT"®, "NYSOSEL®", and "NI 5248 D" (from Engelhard Corporation, Iselin, N.H.). Additional supported nickel hydrogenation catalysts include those commercially available under the trade designations "PRICAT 9910", "PRICAT 9920", "PRICAT 9908", "PRICAT 9936" (from Johnson Matthey Catalysts, Ward Hill, Mass.).

In some embodiments, the hydrogenation catalyst comprising, for example, nickel, copper, palladium, platinum, molybdenum, iron, ruthenium, osmium, rhodium, or iridium. Combinations of metals may also be used. Useful catalyst may be heterogeneous or homogeneous. In some embodiments, the catalysts are supported nickel or sponge nickel type catalysts.

In some embodiments, the hydrogenation catalyst comprises nickel that has been chemically reduced with hydrogen to an active state (i.e., reduced nickel) provided on a support. In some embodiments, the support comprises porous silica (e.g., kieselguhr, infusorial, diatomaceous, or siliceous earth) or alumina. The catalysts are characterized by a high nickel surface area per gram of nickel.

In some embodiments, the particles of supported nickel catalyst are dispersed in a protective medium comprising hardened triacylglyceride, edible oil, or tallow. In an exemplary embodiment, the supported nickel catalyst is dispersed in the protective medium at a level of about 22 wt. % nickel.

Hydrogenation may be carried out in a batch or in a continuous process and may be partial hydrogenation or complete hydrogenation. In a representative batch process, a vacuum is pulled on the headspace of a stirred reaction vessel and the reaction vessel is charged with the material to be hydrogenated (e.g., RBD soybean oil or metathesized RBD soybean oil). The material is then heated to a desired temperature. Typically, the temperature ranges from about 50 deg. C. to 350 deg. C., for example, about 100 deg. C. to 300 deg. C. or about 150 deg. C. to 250 deg. C. The desired temperature may vary, for example, with hydrogen gas pressure. Typically, a higher gas pressure will require a lower temperature. In a separate container, the hydrogenation catalyst is weighed into a mixing vessel and is slurried in a small amount of the material to be hydrogenated (e.g., RBD soybean oil or metathesized RBD soybean oil). When the material to be hydrogenated reaches the desired temperature, the slurry of hydrogenation catalyst is added to the reaction vessel. Hydrogen gas is then pumped into the reaction vessel to achieve a desired pressure of H2 gas. Typically, the H2 gas pressure ranges from about 15 to 3000 psig, for example, about 15 psig to 90 psig. As the gas pressure increases, more specialized high-pressure processing equipment may be required. Under these conditions the hydrogenation reaction begins and the temperature is allowed to increase to the desired hydrogenation temperature (e.g., about 120 deg. C. to 200 deg. C.) where it is maintained by cooling the reaction mass, for example, with cooling coils. When the desired degree of hydrogenation is reached, the reaction mass is cooled to the desired filtration temperature.

The amount of hydrogenation catalysts is typically selected in view of a number of factors including, for example, the type of hydrogenation catalyst used, the amount of hydrogenation catalyst used, the degree of unsaturation in the material to be hydrogenated, the desired rate of hydrogenation, the desired degree of hydrogenation (e.g., as measure by iodine value (IV)), the purity of the reagent, and the H2 gas pressure. In some embodiments, the hydrogenation catalyst is used in an amount of about 10 wt. % or less, for example, about 5 wt. % or less or about 1 wt. % or less.

After hydrogenation, the hydrogenation catalyst may be removed from the hydrogenated product using known techniques, for example, by filtration. In some embodiments, the hydrogenation catalyst is removed using a plate and frame filter such as those commercially available from Sparkler Filters, Inc., Conroe Tex. In some embodiments, the filtration is performed with the assistance of pressure or a vacuum. In order to improve filtering performance, a filter aid may be used. A filter aid may be added to the metathesized product directly or it may be applied to the filter. Representative examples of filtering aids include diatomaceous earth, silica, alumina, and carbon. Typically, the filtering aid is used in an amount of about 10 wt. % or less, for example, about 5 wt. % or less or about 1 wt. % or less. Other filtering techniques and filtering aids may also be employed to remove the used hydrogenation catalyst. In other embodiments the hydrogenation catalyst is removed using centrifugation followed by decantation of the product.

Compositions

The compositions of the invention may be aqueous, preferably substantially aqueous. It has been found that when selecting a composition to be used in hair removal devices, it can be particularly desirable to select a composition which is sufficiently thick and viscous that it will not run off the skin or razor after being dispensed. Additionally, moisturizing compositions can be desirable for use in a fluid dispensing hair removal device to allow for multiple benefits, including but not limited to hydration of the hairs prior to shaving, moisturization of skin during the hair removal process, lubrication of skin to reduce friction during the shave, and so forth. Those of skill in the art will understand that moisturization can include hydration of the skin or hair or occlusion of the skin and or hair, or lubrication of the hair or skin to increase glide and reduce friction between the fluid dispensing device and skin.

Water

The composition of the invention comprises water. In one embodiment, the composition comprises at least about 30% by weight water. In an alternate embodiment, the composition comprises at least about 40% by weight water. In an alternate embodiment, the composition comprises at least about 50%, more preferably at least 60%, even more preferably at least 80% and even more preferably at least 90% by weight water. Compositions having high levels of water enable the device to be used without the necessity for an additional water source to apply or remove the composition from the skin after application.

Additional Components: Silicone Polyether Copolymer

According to the invention, the composition may comprise from about 0.1% to about 60%, preferably from about 0.1% to about 20%, more preferably from about 0.1% to 5%, even more preferably from about 0.1% to about 1% by weight of a silicone polyether copolymer or mixtures thereof.

The silicone polyether copolymer comprises from about 1% to 50%, preferably from 1% to 30%, by weight of polyethylene oxide, from about 20% to about 90%, preferably from 20% to 80% by weight of polypropylene oxide and from about 1% to about 20% by weight of silicone. Preferably the silicone polyether copolymer comprises at least about 40%, more preferably at least about 50%, most preferably at least about 60% by weight of polypropylene oxide. In addition, the silicone polyether copolymer preferably comprises at least about 10%, more preferably from at least about 15%, most preferably from about 15% to 30% by weight of polyethylene oxide. Furthermore, the silicone polyether block copolymer comprises from 1% to 20%, preferably 10% to 20%, more preferably about 15% by weight of silicone.

Whilst silicone polyether block copolymers are known in the art to provide a number of benefits such as foaming, defoaming, wetting, deaeration and lubricity, it has been now been surprisingly found that the selection of silicone block copolymers having from 20% to 90% by weight of polypropylene and from 1% to 50% of polyethylene oxide unexpectedly provide improved lubrication whilst ensuring the required level of water dispersion and or solubility verses silicone polyether block copolymers having less or no polypropylene and more polyethylene oxide. Moreover, the use of such silicone block copolymers provides improved adhesion to the skin verses alternative materials such as copolymers of polyethylene oxide and polypropylene oxide. Furthermore, the inclusion of 1% to 20% of silicone by weight of the silicone polyether block copolymer surprisingly provides desirable levels of lubrication despite being present at low levels in the polymer.

The copolymers are block copolymers and may have a pendant graft structure or a linear structure. The silicone polyether block copolymer comprises from 1% to 50%, preferably from 10% to 30%, more preferably about 20% by weight of polyethylene oxide. The silicone polyether block copolymer comprises from 20% to 90%, preferably from 40% to 80%, more preferably from 50 to 80%, most preferably about 65% by weight of polypropylene oxide. The silicone polyether block copolymer comprises from 1% to 20%, preferably 10% to 20%, more preferably about 15% by weight of silicone.

The silicone polyether block copolymer preferably has a ratio of polyethylene oxide units to polypropylene oxide units of from 3.0 to 0.1, preferably from 2.0 to 0.1, more preferably from 0.6 to 0.25. The silicone polyether block copolymer preferably has a ratio of polyethylene oxide units to polypropylene oxide units to silicone units of from 20:65:15.

The silicone polyether copolymer may have a molecular weight of from about 10000 to about 190000, more preferably from about 10000 to 15000. Suitable silicone polyether copolymers are available from Momentive under the Silwets trademark products including L7210.

In one embodiment the lubricating member comprises silicone polyether block copolymer and a water soluble polymer, preferably polyethylene oxide at a weight ratio of from 1:8 to 8:1, preferably from 1:5 to 5:1, more preferably from 1:3 to 3:1 and even more preferably from 1:2 to 2:1.

In a preferred embodiment the silicone polyether copolymers suitable for use herein only contain repeating units of silicone, polyethylene oxide and polypropylene oxide. Silicone polyether copolymers comprising additional alkyl chains are preferably excluded.

In one embodiment, preferably the silicone polyether block copolymer is sparingly soluble, preferably soluble or more preferably freely soluble in water according to the United States' Pharmacopeia (USP) definition in 31/NF 26 Vol. 2 General Notices, Page Xvii. According to that definition, sparingly soluble means that 30 to 1000 parts of water are needed to dissolve 1 part solute, soluble means that 10 to 30 parts of water are needed to dissolve 1 part solute and freely soluble means than from 1 to 10 parts of water are needed to dissolve 1 part of solute.

The liquid composition comprising the silicone polyether block copolymer as defined in claim 1 and preferably comprising any optional components may have a coefficient of friction as defined according to the method described herein of 0.0300 or less, preferably of 0.0275 or less, more preferably of 0.0250 or less in order to improve lubrication.

Thickening Agent

The composition may contain one or more thickening agents, from about 0.1% to about 5%, alternatively from about 0.1% to about 4%, alternatively from about 0.25% to about 3%, by weight of the composition.

Non limiting classes of thickening agents include those selected from the following: Carboxylic Acid Polymers, Crosslinked Polyacrylate Polymers Polyacrylamide Polymers, Polysaccharides, Clays and Gums, and mixtures thereof when appropriate. In one embodiment, compositions of the present invention include a thickening agent selected from carboxylic acid polymers, crosslinked polyacrylate polymers, polyacrylamide polymers, polysaccharides, and mixtures thereof, more preferably selected from carboxylic acid polymers, polyacrylamide polymers, polysaccharides, and mixtures thereof.

Preferred thickening/suspending agents include electrolyte sensitive polymers that are shear thinning when in solution. Shear thinning is property that makes a liquid easy to spread and pump. We have found that electrolyte sensitive polymers have desired performance profiles. While not wishing to be bound by theory, the electrolyte sensitive polymers interact with the residual surfactant or electrolyte left on the skin and release the lubrication agents and/or suspended conditioning agents for spreading across the razor and across the surface of the skin. Preferred electrolyte sensitive polymers include but are not limited to: Polyacrylamide, Hydroxyethyl Acrylate/Sodium Acryloyldimethyltaurate Copolymer, Sodium Acrylate/Sodium Acryloyldimethyl Taurate Copolymer, Ammonium Polyacrylate, Sodium Acrylate/Acryloyldimethyltaurate/Dimethylacrylamide Crosspolymer, Hydroxyethyl Acrylate/Sodium Acryloyldimethyltaurate Copolymer which can be purchased from Seppic or Carboxylic Acid Polymers (Carbomers) such as Ultrez 10, Carbopol 934, Carbopol 980 and ETD 2050 which can be purchased from Lubrizol or Ammonium Acryloyldimethyltaurate/VP Copolymer, Sodium Acryloyldimethyltaurate/VP Copolymer, Ammonium Acryloyldimethyltaurate/Beheneth-25 Methacrylate Crosspolymer, which can be purchased from Clariant. The most preferred electrolyte sensitive polymer is Polyacrylamide available as Sepigel 305 (Polyacrylamide & C13-14 Isoparaffin & Laureth-7).

Surfactants

The composition may contain one or more surfactants, from about 0.1% to about 20%, alternatively from about 0.5% to about 15%, alternatively from about 1.0% to about 12%, by weight of the composition. Non limiting examples of surfactants for use herein are disclosed in McCutcheon's, Detergents and Emulsifiers, North American edition (1986), published by allured Publishing Corporation; and McCutcheon's, Functional Materials, North American Edition (1992). Preferred surfactants are nonionic surfactants/emulsifiers. Non limiting useful surfactants herein include those selected from the group consisting of alkyl glucosides, alkyl polyglucosides, polyhydroxy fatty acid amides, alkoxylated fatty acid esters, sucrose esters, alkoxylated fatty alcohols, amine oxides, and mixtures thereof. Most preferred are alkoxylated fatty alcohols and alkyl glucosides and mixtures thereof.

In one embodiment the composition comprises less than about 5%, or less than about 3%, or less than about 2% of one or more lathering surfactants or soaps. In one embodiment the composition is free or substantially free of lathering surfactants or soaps. A lathering surfactant is defined as a surfactant which when combined with water and mechanically agitated generate a foam or later. Lathering surfactants include anionic and amphoteric lathering surfactants and mixtures thereof. Anionic lathering surfactants include sarcosinates, sulfates, sulfonate, isethionate, taurates, phosphates, lactylates, glutamates, alkali metal salts of fatty acids (i.e. soaps) having from 8 to 24 carbons, and mixtures thereof.

Lubricants

The compositions may employ one or more additional lubricants, from about 0.1% to about 8%, alternatively from about 0.1% to about 5%, alternatively from about 0.2% to about 3%, by weight of the composition. Exemplary lubricants include lubricous water soluble polymers, water insoluble particles, and hydrogel-forming (or water swellable) polymers, and mixtures thereof.

Examples of suitable water soluble polymers include polyethylene oxide, polyvinyl pyrrolidone, polyacrylamide, polyhydroxymethacrylate, polyvinyl imidazoline, polyethylene glycol, polyvinyl alcohol, polyhydroxyethylmethacrylate, guars, celluloses, modified celluloses and mixtures thereof. In some embodiments, said water soluble polymer is selected from the group consisting of polyethylene oxide, polyethylene glycol, and mixtures thereof.

The preferred water soluble polymers are the polyethylene oxides generally known as POLYOX (available from Union Carbide Corporation) or ALKOX (available from Meisei Chemical Works, Kyoto, Japan). The water soluble polymer, (especially these polyethylene oxides), may have average molecular weights of at least about 20,000, preferably at least about 50,000, more preferably at least about 100,000 or from about 100,000 to about 8 million, preferably from about 300,000 to about 8 million, more preferably from about 1 million to about 5 million, even more preferably about 2 to 3 million. A particularly preferred polyethylene oxide comprises a blend of about 40% to 80% of polyethylene oxide having an average molecular weight of about 5 million (e.g. POLYOX COAGULANT) and about 60% to 20% of polyethylene oxide having an average molecular weight of about 300,000 (e.g. POLYOX WSR-N-750). The polyethylene oxide blend may also advantageously contain up to about 10% (for example about 5%) by weight of a low molecular weight (i.e. MW<10,000) polyethylene glycol such as PEG-100.

Another suitable lubricant is a copolymer of polyethylene oxide (PEO) and polypropylene oxide (PPO). The PEO/PPO copolymer may have an average molecular weight of at least 5,000, preferably in the range of from 10,000 to 20,000, more preferably from 11,000 to 15,000, even more preferably from 12,000 to 13,000 and even more preferably still from 12,250 to 12,750. The PEO/PPO copolymer may advantageously be a block copolymer, preferably a tri-block copolymer having the sequence: PEO-PPO-PEO, the later commercially available under tradenames such as PLURACARA® from BASF and PLURONIC® from Sigma-Aldrich. The PEO/PPO copolymer may have a weight ratio of PEO to PPO (i.e. of ethylene oxide repeat units to propylene oxide repeat units), of from 1000:1 to 1:1000 or from 100:1 to 1:100.

Non limiting useful water insoluble particles may include inorganic particles or organic polymer particles. Hydrogel-forming polymers are typically highly hydrophilic polymers that, in water, form organized three-dimensional domains of approximately nanometer scale. Additional polymer lubricants include: cellulose derivatives such hydroxyalkyl cellulose polymers such as hydroxyethyl cellulose and hydroxypropyl cellulose, carboxymethyl cellulose, and cellulose methyl ether and polysaccharide gums such as, for example, xanthan gum, carrageenan gum, guar gum, locust bean gum, and hydroxypropyl guar gum.

Sensates

In one embodiment of the invention, the composition may contain sensates, or combinations of sensates. Sensates can be materials that provide the sensation of a thermal change, e.g., heating or cooling. Applicants have found that the addition of sensates using this composition provides longer lasting skin sensation and comfort benefits. Non-limiting examples include: p-Methane-3,8-diol; Isopulegol; Menthoxypropane-1,2,-diol; Curcumin; Menthyl Lactate; Gingerol; Icilin; Menthol; Tea Tree Oil; Methyl Salicylate; Camphor; Peppermint Oil; N-Ethyl-p-menthane-3-carboxamide; N-[4-(Cyanomethyl)phenyl]-2-isopropyl-5-methyl-cyclohexane-carboxamide; Ethyl 3-(p-menthane-3-carboxamido) acetate; 2-Isopropyl-N,2,3-trimethylbutyramide; Menthone glycerol ketal, and mixtures thereof.

Optional Ingredients

The composition may further comprise additional optional ingredients. Suitable additional optional ingredients include perfume, preservatives, chelants, sensates (e.g. menthol), desquamation actives, anti-acne actives, anti-wrinkle/anti-atrophy actives, anti-oxidants/radical scavengers, flavonoids, anti-inflammatory agents, anti-cellulite agents, topical anesthetics, tanning actives, skin lightening agents, skin soothing and healing actives, antimicrobial actives, sunscreen actives, visual skin enhancers, humectants and moisturizing agents (e.g., glycerin, glycols, sorbitol), skin feel actives such as cationic polymers and the like. Such optional ingredients are described more fully in U.S. application Ser. No. 11/367,918, filed Mar. 3, 2006. Preferred additional optional ingredients include salicylic acid, opacifiers (e.g. mica and titanium dioxide), perfume, hydrophilic conditioning agents (e.g., glycerin) and skin sensates (e.g. menthol).

Opacifiers may be added to the shave care composition of the present invention. Opacifiers may be either inorganic or organic compounds. Inorganic opacifiers include, for example, titanium dioxide, zinc oxide, talc, mica or coated mica (with oxides of titanium, tin, or iron or bismuth oxychloride), magnesium aluminum silicate, bismuth oxychloride, or other minerals. These compounds can be added as powders, dispersions, or complexes. Organic opacifiers include, for example, opaque emulsions (e.g., containing Styrene/PVP copolymer, vinyl polymers, or latexes), metal salts of amines containing 14-20 carbon atoms per molecule, alkanolamides containing 14-20 carbon atoms per molecule, organic alcohols containing 14-20 carbon atoms per molecule, insoluble salts of stearic acid, glycol mono- or distearates, propylene glycol and glycerol monostearates and palmitates. Combinations of these opacifiers can also be used. The opacifying additive is typically included in an amount of about 1 to about 6%, preferably about 2 to about 5%, by weight of the composition.

For shaving personal care composition embodiments typically applied to the skin before shaving, the compositions may comprise from 40% to 95%, preferably 60% to 95% by weight of water and optionally from 1% to 6% by weight of a volatile post foaming agent. Suitable post foaming agents are selected from aliphatic hydrocarbons having 4 to 6 carbon atoms such as n-pentane, isopentance, neopentane, n-butane, isobutene and mixtures thereof. The personal care compositions may be formulated as aerosol foams, a post foaming gel, a non-aerosol gel or lather and may be packaged in suitable dispenser for dispensing such compositions.

The liquid compositions for use with a hair removal device and or before or after shaving may comprise less than 5%, preferably less than 1% by weight and more preferably is/are substantially free of soap (i.e. salts of fatty C4 to C30 acids) or lathering surfactant as defined hereinabove.

Composition Dispensing Device

The composition dispensing device of the present invention can be any such device which allows the present composition to be dispensed therefrom during the hair removal process. Examples of many types of composition dispensing devices are known. In one embodiment the composition dispensing device is s device having a plurality of shaver heads with rotary blade cutters. In another embodiment, the composition dispensing device is a composition dispensing hair removal device preferably a razor comprising one or more safety razors.

In one embodiment, the device is an automatic vibrating and/or dispensing razors. For example, U.S. 2008-0289185 discloses a razor comprising a fluid delivery system having an electrically actuable dispensing device to control delivery of the fluid, and a control device for controlling actuation of the dispensing device. The control device is in proximity or is touch sensitive and includes a sensor element arranged to be brought into contact with or into close proximity to the skin being shaved during the performance of a shaving stroke. Another suitable device is disclosed in U.S. Pat. No. 7,441,336, which discloses an automated razor which has a control device allowing for automated vibration or dispensing when a certain environmental condition is met, such as proximity or touch with the intended surface or electrical conductance. These types of automated dispensing devices can be particularly useful so that the composition can be dispensed at the desired time onto the skin, thereby minimizing wasted product which could otherwise be captured within the device head or elements thereof. Further, using an automated device may be advantageous as users may have a difficult time deciding when to trigger the dispensing action during the hair removal process. For example, they may accidently trigger the dispensing too early or excessively, causing an undesirably large amount of composition to come out and potentially miss the intended surface for treatment. Automated dispensing, however, is not required, as manual dispensing systems can also be useful for certain purposes.

Non-limiting examples of other composition dispensing devices suitable for use with the present invention include those disclosed in U.S. 2006/00240380 U.S. 2007/0084074; U.S. Pat. Nos. 7,127,817; 7,121,754; and 6,789,321. In some of these examples, the product can be dispensed at or about the vicinity of the device head (commonly a razor cartridge).

In one particularly useful embodiment, the composition can be dispensed through an elongated elastomeric contact region comprising a dispensing orifice which allows the composition to spread in a wide strip onto the surface, such as the lumens described in U.S. 2006/00240380 (see inter alia FIG. 17). Similar dispensing systems have also been described in U.S. Ser. No. 61/340,299 to Royle et al, filed Mar. 15, 2010. The lumens or dispensing orifice can be particularly useful when dispensing the present composition given the specific rheology (thickness and viscosity) desired for use herein. In particular, since the composition is desirably thick and viscous, an elongated dispensing orifice or a plurality of orifices oriented to dispense a wide yet thin layer of the composition may be desired. Advantageously, the layer of composition deposited does not excessively run or drip off the surface prior to the treated surface coming in contact with the razor blade or other hair removal head. Further, where the composition is clear or translucent, the user can easily see where they are shaving so they can have fine control to make clean shaven areas such as a beard line. This can be particularly beneficial over devices comprising shaving heads with rotary blades which would not be as capable of allowing for fine control to make clean shaving lines.

In one embodiment, the composition dispensing device comprises a handle connected to a hair removal head, the handle further comprising a cavity for housing said composition disposed within the handle, and an actuator adapted to displace the composition from the cavity to a fluid dispensing member, and wherein said fluid dispensing member comprises an elongated elastomeric contact region forming at least one dispensing orifice which is generally perpendicular to a transverse centerline of the handle. The fluid dispensing member may extend to or adjacent to the bottom portion of the hair removal head allowing for direct contact or near direct contact to a user's skin during application of the hair removal head to skin, such as during a shaving stroke. The fluid dispensing member comprises a fluid dispensing member comprising at least one elongated elastomeric contact region. In one embodiment, the fluid dispensing member also comprises a one-way valve, which can be formed from said elongated elastomeric contact region. Those of skill in the art will understand that the elastomeric material forming the flap valve, slit valve or duckbill valve is such that upon contact with skin, the valve will deform and allow said one or more dispensing orifice(s) to allow fluid to dispense.

In one embodiment, said elongated elastomeric contact region forms a one-way valve which will only allow the composition to exit so entry of undesirable contaminants into the plumbing or cavity of the device is minimized. Non-limiting examples of suitable one-way valves include: check valves such as diaphragm check valves, swing check valves or tilting disc check valves, stop-check valves, lift-check valves, flap valves, slit valves, and/or a duckbill valve. In one embodiment, the fluid dispensing member forms at least one, but optionally two or more dispensing orifices at the dispensing end of the elongated elastomeric contact member for delivering said fluid from the cavity onto skin prior to hair removal. To prevent the fluid from leaking, the fluid flow path, along with any or all of the dispensing orifice(s) may comprise a check valve.

In another embodiment, the cavity can have multiple compartments. For example the cavity can have a first compartment containing said composition, and wherein said cavity forms a second compartment for a second composition. In another embodiment, the device comprises multiple cavities, where different compositions can be contained therein. In one embodiment, the second composition is selected from the group consisting of an aftershave, a lotion, a balm, a fragrance, or a mixture thereof. Examples of known dispensing devices which allow for multiple compositions to be contained therein include: U.S. Pat. Nos. 6,986,207; 5,855,066; and 4,129,942. In one embodiment, the composition can be used with a device capable of dispensing multiple compositions such as therein described.

Hair Removal Head

The hair removal head can include a wide scraping surface such as where the composition dispensing device is used with a depilatory, or a razor cartridge where the device is a shaving razor. The hair removal head may be replaceable or pivotally connected to a cartridge connecting structure. In an aspect, the cartridge connecting structure includes at least one arm to releasably engage the hair removal head.

Where the hair removal head is a razor cartridge the cartridge may also include multiple blades. For example, U.S. Pat. No. 7,168,173 generally describes a Fusion® razor that is commercially available from The Gillette Company which includes a razor cartridge with multiple blades. Additionally, the razor cartridge may include a guard as well as a shaving aid. A variety of razor cartridges can be used in accordance with the present invention. Nonlimiting examples of suitable razor cartridges, with and without fins, guards, and/or shave aids, include those marketed by The Gillette Company under the Fusion®, Venus® product lines as well as those disclosed in U.S. Pat. Nos. 7,197,825, 6,449,849, 6,442,839, 6,301,785, 6,298,558; 6,161,288, and U.S. 2008/060201.

Fluid Dispensing Member

The fluid dispensing member may comprise an elongated elastomeric contact region. Non-limiting examples of suitable elongated elastomeric contact regions include: dual slit or duckbill valves such as those described in U.S. 2006/00240380 in FIGS. 1-9 and paragraphs 52 to 58. The present invention, however, does not require dual lumens to be present. Further, the present fluid dispensing member is designed to deliver fluid away from, preferably preceding, the head area of the devices disclosed in the art. By delivering fluid prior to the skin contacting the hair removal head, it allows for broader spreading of the fluid and additional time where the fluid can come into contact with the folds and crevices within the skin. In one embodiment, the fluid dispensing member further comprises a non-elastomeric portion which can precede said elongate elastomeric contact member. The non-elastomeric portion can be formed of the same material as used to form any part of the remainder of the handle. In one embodiment, the one-way valve is not formed in said elongated elastomeric contact member. The one-way valve can be formed in the non-elastomeric portion of said fluid dispensing member or in any portion of said fluid flow path, such as in the supply channel, at the opening, and/or in the fluid dispensing path.

"Elongated" as defined herein means, that the object has a major and a minor axis, wherein the major axis is at least 10 times larger than the minor axis. The elongated portion of the fluid dispensing member has a width (major axis) which is at least 10 times larger than the height. In one embodiment, the width measures from about 2 cm to about 15 cm, alternatively from about 3 cm to about 10 cm, alternatively from about 4 cm to about 8 cm. In another embodiment, the height of the elongated one-way elastomeric valve is about 1 cm, alternatively about 0.5 cm, alternatively from about 0.2 cm, alternatively the elongated one-way elastomeric valve is biased to be in a sealed orientation when not in use.

Those of ordinary skill in the art will understand that a check valve may be used in embodiments where the elongated one-way elastomeric valve is not sealed when not in use to minimize product leakage. In another embodiment, the fluid is chosen such that even if the height of the valve is such that it remains unsealed and open when not in use, the fluid is sufficiently viscous and thick that it will not undesirably leak when not being actuated by the user.

"Elastomeric" as defined herein means a material which is generally flexible and deformable. In one embodiment, the elongated elastomeric contact member has a young's modulus of elasticity of from about 0.01 GPa to about 3.5 GPa, alternatively from about 0.02 GPa to about 2 GPa, alternatively from about 0.05 GPa to about 1 GPa, alternatively from about 0.1 GPa to about 0.5 GPa. Non-limiting examples of suitable materials which can be used to form the elastomeric contact member include rubber, silicone, Teflon, and polyethylene. Without intending to be bound by theory, it is believed that by providing an elastomeric material in the fluid dispensing member at the point where the fluid dispensing member would contact skin is particularly useful as it decreases irritation onto skin from a non-elastomeric fluid dispensing member. Further, the elastomeric material allows the tip of the fluid dispensing member to deform to better engage the non-symmetric shape of body parts. In one embodiment, the elastomeric material used has a shore hardness of from about 30 to about 40 D units.

"Slit valve" as defined herein means that the valve comprises a closed slit and flow is provided by flexing or deformation of the elastomeric material which causes the slit to open. In general the slit valve is a single piece construction which is free of moving parts. "Duckbilled valve" as defined herein is a type of slit valve, wherein one end of the valve is stretched over the outlet of the fluid dispensing path, conforming itself to the shape of the path, usually round. The other end, the duckbill, retains a natural flattened shape. When a fluid is pumped through the fluid dispensing path, the duckbill's flattened end opens to permit the pressurized fluid to pass. When pressure is removed, however, the duckbill end returns to its flattened shape, preventing backflow. Other check valves referred to herein are known in the art.

"Generally perpendicular" as defined herein means that the lateral dimension of the elongated elastomeric contact region forms an angle which is from about 75° to about 90° as measured against the transverse centerline passing through the handle. Since the elongated elastomeric contact region is generally elastic and therefore deformable in nature, this angle is measured when the fluid dispensing region is at rest and not deformed or otherwise manipulated by a user. The elongated elastomeric contact region comprises a contact point where the fluid dispensing member engages the surface (skin). In one embodiment, the contact point forms a straight line. In another embodiment, the contact point forms a concave or convex line. Similarly, "generally parallel" as defined herein means that the two straight lines formed through said objects are parallel or form an angle of from about 0° to about 15° when in a resting position.

The fluid flow path terminates at least one fluid dispensing orifice. In one embodiment, more than one fluid dispensing orifice is provided. The fluid dispensing orifice is formed of the elastomeric material used to form the elongated elastomeric contact member. Preferably, the fluid dispensing orifice has a wide and narrow shape similar to the fluid dispensing member but the fluid dispensing orifice can also be of different shapes. In one embodiment, the fluid dispensing member comprises a plurality of fluid dispensing orifices which are spaced out along the width of the elongated elastomeric contact member such that when fluid is dispensed, a wide flat application of fluid can still be deposited. The fluid dispensing orifices can be round, oval, triangular, square, rectangular in shape, or combinations thereof. In one embodiment, the portion of the elongated elastomeric contact member leading up to the fluid dispensing orifice forms a tapered exit channel, the tapering can be tapered in, or tapered out. Without intending to be bound by theory, it is believed that a tapered exit channel, particularly one that tapers out so the cross sectional area of the orifice is larger than the cross sectional area of the channel leading to the orifice, can be useful to ease in removal of any fluid which can reside in the vicinity of the orifice after use. A tapered in exit channel may be useful to minimize exposure of the fluid to contact with air, thereby minimizing fluid dry out.

Actuator

As explained above, the actuator can be manual or automatic pump (battery powered or via an external power source). The pump includes a wall, either movable or rigid, upon which force is acted upon to move the fluid through. In the case of a movable wall, the movable wall may be located on one or more of an upper or lower surface of the handle. For a rigid wall, the force causes the movement of non-rigid sidewalls of the pump to move a fluid through to the channel.

In one embodiment, the actuator is a manually-actuated pump which can reside on the handle. In another embodiment, the actuator is automated and can be powered by a battery or external power source. In yet further embodiments, the actuator comprises a pump which is actuated by movement of the shaving head (such as where depression of the head or rotation of the head about the pivot axis), actuates the pump. In yet another embodiment, the fluid dispensing member itself can be spring loaded and retractable upon contact with a surface such as skin such that the movement of the fluid dispensing member can act as the actuation to actuate the pump. Those of skill in the art will understand that in this type of embodiment, it could be preferred to have the elongated elastomeric contact region extend beyond the general plane of the shaving head such that when the device is brought into contact with a surface (such as skin) the fluid dispensing member will be pushed back towards the razor prior to surface contact with the shaving head. The movement of the fluid dispensing member can then actuate the pump permitting fluid to escape or be driven out of the cavity through the fluid flow path, out of the at least one dispensing orifice, ultimately onto the skin.

In one embodiment the composition dispensing device includes a handle and a hair removal head, such as a disposable razor cartridge. The composition dispensing device can be a wet or dry, manual or powered razor, having straight or rotary blades. In addition, the composition dispensing device can be used with a depilatory, therefore not requiring the use of razor. The handle has a length that extends from a proximal end to a distal end and a transverse centerline which runs along the central axis of the handle. The handle comprises a cavity for housing a fluid disposed within the handle, and an actuator adapted to displace the fluid from the cavity preferably through a supply channel to an opening formed in said handle, such as towards the proximal end of the handle.

The composition dispensing device may include a fluid dispensing member comprising an elongated elastomeric contact region forming at least one dispensing orifice in fluid communication with said opening formed in said handle. Said elongated elastomeric contact region comprises a lateral dimension, which is generally perpendicular to said transverse centerline of the handle. The hair removal head also has a lateral dimension which his generally perpendicular to said transverse centerline. In one embodiment, the ratio of the lateral dimension of the elongated elastomeric contact region to the lateral dimension of the hair removal head is from 1:10 to about 1.5:1, alternatively from about 0.5:1 to about 1:1. Without intending to be bound by theory, it is believed that by providing an elongated elastomeric contact region which is laterally sized with respect to the hair removal head as recited herein, the fluid dispensed from said at fluid dispensing member covers a sufficiently broad portion of said hair removal head to provide suitable product spreading over skin and into cracks and corners of the skin. The fluid dispensing member is in fluid communication with said cavity via said opening, forming a fluid dispensing path, wherein said supply channel and said fluid dispensing path form a fluid flow path.

In one embodiment, the device includes at least one, one-way valve located at some point along said fluid flow path. As explained above, in some embodiments, said elongated elastomeric contact point forms said one-way valve. Additional one-way valves can also be included along the fluid flow path as desired.

The actuators are typically manual pumps but automatic pumps can also be included. The actuators, which can be manual or automatic, and may include pumps which can be stacked (and substantially flat) components and particularly a movable wall that acts to activate the flow of fluid from the cavity through channel and to the opening. A pump suitable for use in the present invention is disclosed in U.S. Pat. No. 5,993,180. In particular, this pump includes a pump chamber bounded by the movable wall, an inlet channel and an outlet channel, both of which are connected to the pump chamber, an inlet valve for closing the inlet channel, and an outlet valve for closing the outlet channel. In most instances, the pump may be actuated by the pressure exerted by a user's finger such that the user may easily determine the requisite amount of fluid for one or more shaving strokes. Because the valves of the pump are automatically opened when pressure is applied by the user's finger pressure, the fluid can be dispensed in controlled and metered quantities without relying on judgment or dexterity of the user. It is also possible to place one or more movable walls of the pump on an upper surface or lower surface of the razor depending on a user's preference. The actuator provides a feed into the cavity. This feed can be application of pressure or another impulse which will drive fluid through said fluid flow path out to the fluid dispensing member. The actuator may alternatively has a receiving chamber where fluid is transferred prior to entering the supply channel and passing into the fluid dispensing member. These and other actuators and pumps which are known in the art for use in personal care devices which dispense fluids can be used in accordance with the present invention.

The cavity or at least a container/sachet within the cavity contains the fluid to be dispensed during the hair removal process. In one embodiment, the fluid in the cavity or container is refillable or replaceable.

In another embodiment fluid dispensing member is pivotably attached to said handle via a hinge member positioned on said handle. In one embodiment, a portion of the fluid flow path, such as the fluid dispensing path can be exposed upon exiting said opening formed in said handle.

In another embodiment of the composition dispensing device, the fluid dispensing member may deform. The fluid dispensing member may extend beyond the general facial plane formed by said hair removal head. Since the fluid dispensing member comprises an elastomeric contact region, the portion of the fluid dispensing member which extends beyond the plane of the hair removal head would deform, when the device comes in contact with a surface, such as skin. A fluid dispensing member is deformed when the device is in an "in-use" position, allowing fluid to exit the at least one dispensing orifice formed in the elongated elastomeric contact region. The elongated elastomeric contact region can flex toward the hair removal head, flex away from the hair removal head and can even come into contact with a portion of the hair removal head, all depending on the movement of the device with respect to the surface. A volume of fluid is deposited onto the skin and the hair removal head is moved in a downward trajectory along the skin to remove hairs which have been treated with said fluid. Further, the one-way valve shown is positioned along the fluid flow path but not at the point where the fluid dispensing member forms said at least one dispensing orifice.

In one embodiment, the cartridge attaches to the rear surface of a housing by a cartridge connecting structure. The cartridge connecting structure may include one or more arms that extend to provide pivotal support of the housing. Alternatively, the cartridge connecting structure may include an ejection mechanism (e.g., a button) to disengage the housing from the cartridge connecting structure. Non-limiting examples of suitable housings and cartridge connecting structures are described in: U.S. Pat. Nos. 7,197,825, 5,822, 869, 6,161,287, and 5,784,790.

The razor cartridge may also include a guard and or lubricating strip. The guard is useful for stretching the skin's surface immediately prior to engagement with the blade or a first blade (when more than one blade is present). This guard may typically comprise an elastomeric member to allow for an engagement that is comfortable to a user. Typically, the elastomeric material used is a block copolymer (or other suitable materials), preferably having a durometer between 28 and 60 Shore A.

The lubricating strip, on the other hand, provides an additional treatment to the skin after contact between the fluid and the skin has occurred. The lubricating strip may contain the same or additional skin ingredients to those that are present in the fluid. The cartridge connecting structure may be releasably engaged from the handle, as disclosed for example in U.S. Pat. D533,684, 5,918,369, and 7,168,173. This disengagement of these two components allows for replacement of razor cartridges as the continued use of such cartridges causes blade dulling. Thus, such cartridges are replaceable and disposable at will by the user.

In another embodiment the hair removal head is a razor cartridge with a plurality of blades and a lubricating strip shaving aid as well as a guard. The razor cartridge may have a lateral dimension which can measure any length typically used for conventional straight blade wet razor cartridges, for example from about 2 cm to about 10 cm, alternatively from about 3 cm to about 8 cm, alternatively from about 4 cm to about 7 cm. Said elongated elastomeric contact region comprises a lateral dimension which is generally perpendicular to said transverse centerline of the handle. In this embodiment, the device comprises two fluid dispensing orifices. Those of skill in the art will understand that different fluid dispensing orifice configurations are within the scope of the invention. The two fluid dispensing orifices may be equal in length and are positioned linear to one another. The lengths can vary and the orifices can be staggered so they do not sit on the same line. Further, although the at least one fluid dispensing orifice is generally parallel to the angle of the razor cartridge and/or blades, the orifice can be angled. The lateral dimension of the at least one fluid dispensing orifice is measured as the greatest lateral distance covered by the orifice, regardless of the angle upon which the orifice sits with respect to the razor cartridge and/or blades. In another embodiment, the at least one fluid dispensing orifice can have a curved or wavy line shape. In one embodiment, the ratio of the lateral dimension of the at least one fluid dispensing orifice to the lateral dimension of the hair removal head is from about 1:10 to about 1:1, alternatively from about 1:5 to about 1:2.

In one embodiment the elongated elastomeric contact member is with a transverse central axis. The elongated elastomeric contact member, being deformable and elastic in nature can twist, bend, compress and stretch as needed. In this embodiment, the elongated elastomeric contact member has a rotation path showing the ability of the elongated elastomeric contact member to rotate about said transverse central axis. In this embodiment, the portion of the elongated elastomeric contact member which forms the at least one fluid dispensing orifice is in a sealed position, and has a greater lateral dimension than the portion of the elongated elastomeric contact member which would be closer to the handle. Those of skill in the art will understand that the elongated elastomeric contact member can have a constant, increasing or decreasing lateral dimension as the lateral dimension is measured from the distal end to the proximal end (towards the handle).

In another embodiment, both the tip of the fluid dispensing member and the at least one fluid dispensing orifice are concave shaped so they can contour to body parts easier. The at least one fluid dispensing orifice has a lateral dimension. This could be particularly preferable for female composition dispensing devices which are designed for use on the leg or arms. In this embodiment, the hair removal head has a scraping edge. The hair removal head can also be a razor cartridge as described above.

In one embodiment, the hair removal head has a skin contacting edge which is flat, concave or convex. Those of skill in the art will understand that different shapes for the skin contacting edge can be preferred based on the desired part of the body upon which the device is intended for use. For example, a composition dispensing device intended for use on the face may have an applicator having a straight edge. A composition dispensing device intended for use on legs may have an applicator having a concave edge. Non-limiting examples of suitable head configurations are disclosed in U.S. Pat. Nos. D399,601, D203,892, and 651,420; U.S. Pat. Nos. 3,088,470, 3,858,985, and U.S. 2004 0168743A1; WO 97/18043A1 and GB1390153.

In another embodiment the fluid dispensing member has an angled and tapered distal region (extending away from the handle). A fluid dispensing orifice is in fluid communication with the fluid flow path. In one embodiment, a check valve is provided along the fluid flow path. In another embodiment, the fluid dispensing orifice can include a flap or be designed to close when not in use. The fluid dispensing orifice could then act as a one-way valve as described above. In one embodiment the fluid flow path has a constant cross sectional area or a varying cross sectional area. The fluid flow path is tapered as it approaches the fluid dispensing orifice.

In one embodiment, the fluid dispensing orifice has a width of from about 2 cm to about 15 cm, alternatively from about 3 cm to about 10 cm, alternatively from about 4 cm to about 8 cm. Where numerous fluid dispensing members are provided, the width can be even smaller, as low as about 0.2 cm, or about 0.5 cm, or about 1 cm. The width of the fluid dispensing orifice is preferably 0 cm when the device is in a sealed state (not in use) but the width can change when the orifice is opened and can be from about 0.02 cm to about 0.5 cm, alternatively from about 0.05 cm to about 0.3 cm, alternatively from about 0.1 cm to about 0.2 cm. In one embodiment, the fluid dispensing orifice is not 0 cm when not in use. In this embodiment, a check valve can be included somewhere along the fluid flow path to control movement of the fluid before it reaches the fluid dispensing orifice. In another embodiment, the fluid dispensing orifice comprising a width of from about 0.5 mm to about 10 mm, or from about 1 mm to about 3 mm, and a length of from about 20 mm to about 80 mm, or from about 30 mm to about 70 mm, alternatively from about 40 mm to about 50 mm.

Methods of Use

As explained above, the present device is designed for use in the hair removal process, such as when shaving. One embodiment of the present invention provides for a method of removing hair from skin comprising the steps of: providing a composition dispensing device containing the composition described herein; actuating said composition dispensing device to dispense said composition; contacting said composition onto a portion of skin to be treated to form a prepared surface; and contacting said prepared surface with the composition dispensing device to form a treated surface.

Another embodiment further comprises a step of wetting said portion of skin to be treated either before contacting said composition onto a portion of skin or after contacting said prepared surface with the composition dispensing device to form a treated surface. The process can also include a step of leaving the treated surface as is, without further washing or rinsing, after the hair removal step.

In another embodiment, the composition is dispensed from the device directly onto skin from the dispensing member of said composition dispensing device. This step can be by manually triggering an actuator, or by an automated control device which senses when the device is in proximity or in contact with the surface to be treated. The composition could also be dispensed onto a portion of the device which is then contacted to the skin to apply the composition but this is not necessary where dispensing directly on to skin is possible.

In yet another embodiment, the steps of contacting said composition onto the skin and contacting said treated surface with the razor blade can occur simultaneously.

In one embodiment, the device is used in a dry shave context where water or other shave preparations are not used to pre-wet the skin. Water can still be used, however, after the dry shave to wash of any shave debris and remaining moisturizing composition. Yet another embodiment provides for a further step of applying a second skin care composition onto the treated surface, such as a post-shave composition. These and other methods of use of the present device in a grooming context are within the scope of the present invention.

TEST METHODS

Molecular Weight Distribution

The weight average molecular weight (Mw) is measured using gel permeation chromatography (GPC) and multi-angle laser light scattering (MALLS). The GPC/MALLS system used for the analysis is comprised of a Waters Alliance e2695 Separations Module, a Waters 2414 interferometric refractometer, and a Wyatt Heleos II 18 angle laser light scattering detector. The column set used for separation is purchased from TOSOH Biosciences LLC, King of Prussia, Pa. and included: Guard Column TSKgel G1000Hx-GMHx1-L (Cat #07113), TSKgel G3000Hx1 (Cat #0016136), TSKgel G2500Hx1 (Cat #0016135), and TSKgel G2000Hx1 (Cat #0016134). Wyatt ASTRA 6 software was used for instrument operation and data analysis. The 90 degree light scattering detection angle is calibrated using filtered, anhydrous toluene. The remaining detection angles are normalized using an isotropic scatterer in THF. To verify instrument performance of the MALLS and RI (refractive index) detectors, a poly(styrene) standard with a known Mw and known dn/dc (in the mobile phase) is run. Acceptable performance of the MALLS and RI detectors gives a calculated Mw within 5% of the reported Mw of the poly(styrene) standard and a mass recovery between 95 and 105%.

To complete the GPC/MALLS analysis, a value of dn/dc is needed. The value of dn/dc is measured as follows. The RI detector is thermostated to 35 degrees Celsius. A series of five concentration standards of the metathesized unsaturated polyol ester in THF is prepared in the range 0.5 mg/ml to 5.5 mg/ml. A THF blank is injected directly into the refractive index detector, followed by each of the metathesized unsaturated polyol ester concentration standards, and ending with another THF blank. The volume of each sample injected is large enough to obtain a flat plateau region of constant differential refractive index versus time; a value of 1.0 ml is typically used. In the ASTRA software, a baseline is constructed from the initial and final THF injections. For each sample, peak limits are defined and the concentrations entered to calculate dn/dc in the ASTRA software. For the metathesized canola oil of Example 2 in THF, a dn/dc value of 0.072 ml/g is obtained.

For the GPC/MALLS analysis of a metathesized unsaturated polyol ester, a total of three samples are evaluated: the metathesized unsaturated polyol ester, a non-metathesized unsaturated polyol ester (glycerol trioleate [122-32-7], Sigma-Aldrich, Milwaukee, Wis.), and a representative olefin (1-octadecene, [112-88-9], Sigma-Aldrich, Milwaukee, Wis.). The GPC samples are dissolved in tetrahydrofuran (THF). Concentrations for the metathesized unsaturated polyol ester are approximately 20 mg/ml, and concentrations for the non-metathesized unsaturated polyol ester and olefin are approximately 5 mg/ml. After all the material is dissolved, each solution is filtered by a 0.45 micron nylon filter disk into a GPC autosampler vial for analysis. The GPC column temperature is at room temperature, approximately 25 degrees Celsius. HPLC grade THF is used as the mobile phase and is delivered at a constant flow rate of 1.0 ml/min. The injection volume is 100 microliters and the run time is 40 minutes. Baselines are constructed for all signals. Peak elution limits include metathesized unsaturated polyol ester and non-metathesized unsaturated polyol ester, but exclude later eluting residual olefin. The retention times of the non-metathesized unsaturated polyol ester and olefin were determined from the separate injection runs of both the non-metathesized unsaturated polyol ester and olefin. Baselines and scattering detectors are reviewed.

Oligomer Index

The oligomer index of the metathesized unsaturated polyol ester is calculated from data that is determined by Supercritical Fluid Chromatography-Fourier Transform Orbital Trapping Mass Spectrometry (SFC-Orbitrap MS). The sample to be analyzed is typically dissolved in methylene chloride or a methylene chloride-hexane mixture at a concentration of 1000 ppm (1 mg/mL). A further 25×-100× dilution is typically made into hexane (for a final concentration of 10-40 ppm). A volume of 2-7.5 μL is typically injected on to a SFC column (for example, a commercially available 3 mm i.d.×150 mm Ethylpyridine column, 3 μM particle size).

During the chromatography run, the mobile phase is typically programmed from 100% carbon dioxide with a gradient of one percent per minute methanol. The effluent from the column is directed to a mixing tee where an ionization solution is added. The ionization medium is typically 20 mM ammonium formate in methanol at a flow of 0.7 mL/min while the SFC flow is typically 1.6 mL/min into the tee. The effluent from the mixing tee enters the ionization source of the Orbitrap Mass Spectrometer, which is operated in the heated electrospray ionization mode at 320° C.

In one aspect, a hybrid linear ion trap-Orbitrap mass spectrometer (i.e., the Orbitrap Elite from Thermoelectron Corp.) is calibrated and tuned according to the manufacturer's guidelines. A mass resolution (m/Δm peak width at half height) from 100,000 to 250,000 is typically used. C,H,O compositions of eluting species (typically associated with various cations, e.g., $NH_4^+$, $H^+$, $Na^+$) are obtained by accurate mass measurement (0.1-2 ppm) and are correlated to metathesis products. Also, sub-structures may be probed by linear ion trap "MS" experiments with subsequent accurate-mass analysis in the Orbitrap, as practiced typically in the art.

The metathesis monomers, dimers, trimers, tetramers, pentamers, and higher order oligomers are fully separated by SFC. The chromatogram based on ion current from the Orbitrap MS may be integrated, as typically practiced in the art, for each of the particular oligomer groups including metathesis monomers, metathesis dimers, metathesis trimers, metathesis pentamers, and each of the higher order oligomers. These raw areas may then be formulated into various relative expressions, based on normalization to 100%. The sum of the areas of metathesis trimers through the highest oligomer detected is divided by the sum of all metathesis species detected (metathesis monomers to the highest oligomer detected). This ratio is called the oligomer index. As used herein, the "oligomer index" is a relative measure of the fraction of the metathesized unsaturated polyol ester which is comprised of trimers, tetramers, pentamers, and higher order oligomers.

Iodine Value

Another aspect of the invention provides a method to measure the iodine value of the metathesized unsaturated polyol ester. The iodine value is determined using AOCS Official Method Cd 1-25 with the following modifications: carbon tetrachloride solvent is replaced with chloroform (25 ml), an accuracy check sample (oleic acid 99%, Sigma-Aldrich; IV=89.86±2.00 cg/g) is added to the sample set, and the reported IV is corrected for minor contribution from olefins identified when determining the free hydrocarbon content of the metathesized unsaturated polyol ester.

Free Hydrocarbon Content

Another aspect of this invention provides a method to determine the free hydrocarbon content of the metathesized unsaturated polyol ester. The method combines gas chromatography/mass spectroscopy (GC/MS) to confirm identity of the free hydrocarbon homologs and gas chromatography with flame ionization detection (GC/FID) to quantify the free hydrocarbon present.

Sample Prep: The sample to be analyzed was typically trans-esterified by diluting (e.g. 400:1) in methanolic KOH (e.g. 0.1N) and heating in a closed container until the reaction was complete (i.e. 90° C. for 30 min.) then cooled to room temperature. The sample solution could then be treated with 15% boron tri-fluoride in methanol and again heated in a closed vessel until the reaction was complete (i.e. at 60° C. for 30 min.) both to acidify (methyl orange-red) and to methylate any free acid present in the sample. After allowing to cool to room temperature, the reaction was quenched by addition of saturated NaCl in water. An organic extraction solvent such as cyclohexane containing a known level internal standard (e.g. 150 ppm dimethyl adipate) was then added to the vial and mixed well. After the layers separated, a portion of the organic phase was transferred to a vial suitable for injection to the gas chromatograph. This sample extraction solution was analyzed by GC/MS to confirm identification of peaks matching hydrocarbon retention times by comparing to reference spectra and then by GC/FID to calculate concentration of hydrocarbons by comparison to standard FID response factors.

A hydrocarbon standard of known concentrations, such as 50 ppm each, of typically observed hydrocarbon compounds (i.e. 1-dodecene, 1-tridecene, 1-tetradecene, 1-pentadecene, 1-hexadecene, 1-heptadecene, 1-octadecene, dodecane, tridecane, tetradecane, pentadecane, hexadecane, heptadecane and octadecane) was prepared by dilution in the same solvent containing internal standard as was used to extract the sample reaction mixture. This hydrocarbon standard was analyzed by GC/MS to generate retention times and reference spectra and then by GC/FID to generate retention times and response factors.

GC/MS: An Agilent 7890 GC equipped with a split/splitless injection port coupled with a Waters QuattroMicroGC mass spectrometer set up in EI+ ionization mode was used to carry out qualitative identification of peaks observed. A non-polar DB1-HT column (15 m×0.25 mm×0.1 um df) was installed with 1.4 mL/min helium carrier gas. In separate runs, 1 uL of the hydrocarbon standard and sample extract solution were injected to a 300° injection port with a split ratio of 25:1. The oven was held at 40° C. for 1 minute then ramped 15 C.°/minute to a final temperature of 325° C. which was held for 10 minutes resulting in a total run time of 30 minutes. The transfer line was kept at 330° C. and the temperature of the EI source was 230° C. The ionization energy was set at 70 eV and the scan range was 35-550 m/z.

GC/FID: An Agilent 7890 GC equipped with a split/splitless injection port and a flame ionization detector was used for quantitative analyses. A non-polar DB1-HT column (5 m×0.25 mm×0.1 um df) was installed with 1.4 mL/min helium carrier gas. In separate runs, 1 uL of the hydrocarbon standard and sample extract solution was injected to a 330° injection port with a split ratio of 100:1. The oven was held at 40° C. for 0.5 minutes then ramped at 40 C.°/minute to a final temperature of 380° C. which was held for 3 minutes resulting in a total run time of 12 minutes. The FID was kept at 380° C. with 40 mL/minute hydrogen gas flow and 450 mL/min air flow. Make up gas was helium at 25 mL/min. The hydrocarbon standard was used to create a calibration table in the Chemstation Data Analysis software including known concentrations to generate response factors. These response factors were applied to the corresponding peaks in the sample chromatogram to calculate total amount of free hydrocarbon found in each sample.

EXAMPLES

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Non-limiting examples of product formulations disclosed in the present specification are summarized below.

Example 1: Synthesis of Metathesized Canola Oil

Prior to the metathesis reaction, the RBD (refined, bleached, and deodorized) canola oil is pre-treated by mixing the oil with 2% (by weight) bleaching clay (Filtrol F-160, BASF, Florham Park, N.J.) and heating to 120° C. with a nitrogen sweep for 1.5 hours. The oil is cooled to room temperature, filtered through a bed of CELITE® 545 diatomaceous earth (EMD, Billerica, Mass.), and stored under inert gas until ready to use.

To a round-bottomed flask, the oil is added and sub-surface sparged with inert gas while mixing and heating to 55° C. The catalyst is dissolved in 1,2-dichloroethane ([107-06-2], EMD, Billerica, Mass.) that is stored over 4 Å molecular sieves and sub-surface sparged with inert gas prior to use. After catalyst addition to the reaction flask, a vacuum is applied to remove volatile olefins that are generated. After ~4 hours reaction time, the vacuum is broken and the metathesized unsaturated polyol ester is cooled to room temperature.

The metathesized canola oil is diluted in hexanes ([110-54-3], EMD, Billerica, Mass.). To the diluted material, 2% bleaching clay (Filtrol F-160, BASF, Florham Park, N.J.) is added and mixed for ~6 hours. The oil is filtered through a bed of CELITE® 545 diatomaceous earth. The oil is treated a second time with 2% bleaching clay (Filtrol F-160, BASF, Florham Park, N.J.) for ~6 hours. The oil is filtered through a bed of CELITE® 545 diatomaceous earth and then rotary evaporated to concentrate.

The metathesized canola oil is then passed through a wipe film evaporator at 180° C. and <0.5 Torr vacuum to remove olefins up to and including C-18 chain lengths. Representative examples are summarized in the table below.

| Example | Pretreated Canola Oil (g)[a] | Catalyst | Catalyst (g) | Max Temperature (° C.) | Max Vacuum (Torr) |
|---|---|---|---|---|---|
| 1A | 500 | 1[b] | 0.25 | 61 | 7.9 |
| 1B | 500 | 2[c] | 0.25 | 62 | 0.6 |

[a]Canola oil from J. Edwards, Braintree, MA.
[b]Tricyclohexylphosphine [4,5-dimethyl-1,3-bis(2,4,6-trimethylphenyl)imidazol-2-ylidene] [2-thienylmethylene]ruthenium (II) dichloride [1190427-50-9] available as CatMETium RF-3 from Evonik Corporation, Parsippany, NJ.
[c]Tricyclohexylphosphine[1,3-bis(2,4,6-trimethylphenyl)imidazol-2-ylidene][2-thienylmethylene] ruthenium(II) dichloride [1190427-49-6] available as CatMETium RF-2 from Evonik Corporation, Parsippany, NJ.

The samples 1A and 1B are analyzed for weight average molecular weight, iodine value, free hydrocarbon content and oligomer index, using methods described previously, and are found to approximately have the following values:

| Example | Mw (g/mol) | Iodine Value (cg/g) | Free Hydrocarbon content (wt %) | Oligomer Index |
|---|---|---|---|---|
| 1A | 5,400 | 85 | 0.5 | 0.05 |
| 1B | 3,900 | 85 | 0.5 | 0.04 |

Example 2: Remetathesis of Metathesized Unsaturated Polyol Ester

Metathesized canola oil, sufficiently stripped of residual olefins (176.28 g from Example 1A) is blended with pre-treated canola oil (350.96 g, pretreated as described in Example 1) in a round-bottomed flask. The blend is sub-surface sparged with inert gas while mixing and heating to 55° C. The catalyst is dissolved in 1,2-dichloroethane ([107-06-2], EMD, Billerica, Mass.) that is stored over 4 Å molecular sieves and sub-surface sparged with inert gas prior to use. After catalyst addition to the reaction flask, a vacuum is applied to remove volatile olefins that are generated. After ~4 hours reaction time, the vacuum is broken and the metathesized unsaturated polyol ester is cooled to room temperature.

The metathesized canola oil is diluted in hexanes ([110-54-3], EMD, Billerica, Mass.). To the diluted material, 2% bleaching clay (Filtrol F-160, BASF, Florham Park, N.J.) is added and mixed for ~6 hours. The oil is filtered through a bed of CELITE® 545 diatomaceous earth. The oil is treated a second time with 2% bleaching clay (Filtrol F-160, BASF, Florham Park, N.J.) for ~6 hours. The oil is filtered through a bed of CELITE® 545 diatomaceous earth and then rotary evaporated to concentrate.

The remetathesized canola oil is then passed through a wipe film evaporator at 180° C. and <0.5 Torr vacuum to remove olefins up to and including C-18 chain lengths. A representative example is summarized in the table below.

| Example | Oil Blend (g) | Catalyst[a] (g) | Max Temperature (° C.) | Max Vacuum (Torr) |
|---|---|---|---|---|
| 2 | 500 | 0.27 | 65 | 0.2 |

[a]Tricyclohexylphosphine [4,5-dimethyl-1,3-bis(2,4,6-trimethylphenyl)imidazol-2-ylidene] [2-thienylmethylene]ruthenium (II) dichloride [1190427-50-9] available as CatMETium RF-3 from Evonik Corporation, Parsippany, NJ.

The sample 2 is analyzed for weight average molecular weight, iodine value, free hydrocarbon content and oligomer index, using methods described previously, and is found to approximately have the following values:

| Example | Mw (g/mol) | Iodine Value (cg/g) | Free Hydrocarbon content (wt %) | Oligomer Index |
|---|---|---|---|---|
| 2 | 13,000 | 80 | 0.5 | 0.07 |

Example 3: Synthesis of Metathesized Unsaturated Polyol Esters

Prior to the metathesis reaction, the RBD (refined, bleached, and deodorized) oil is pre-treated by mixing the oil with 2% (by weight) bleaching clay (Filtrol F-160, BASF, Florham Park, N.J.) and heating to 120° C. with a nitrogen sweep for 1.5 hours. The oil is cooled to room temperature, filtered through a bed of CELITE® 545 diatomaceous earth (EMD, Billerica, Mass.), and stored under inert gas until ready to use.

To a round-bottomed flask, the oil is added and sub-surface sparged with inert gas while mixing and heating to 55° C. The catalyst is dissolved in 1,2-dichloroethane ([107-06-2], EMD, Billerica, Mass.) that is stored over 4 Å molecular sieves and sub-surface sparged with inert gas prior to use. After catalyst addition to the reaction flask, a vacuum is applied to remove volatile olefins that are generated. After ~4 hours reaction time, the vacuum is broken and the metathesized unsaturated polyol ester is cooled to room temperature.

The metathesized oil is diluted in hexanes ([110-54-3], EMD, Billerica, Mass.). To the diluted material, 2% bleaching clay (Filtrol F-160, BASF, Florham Park, N.J.) is added and mixed for ~6 hours. The metathesized oil is filtered through a bed of CELITE® 545 diatomaceous earth. The metathesized oil is treated a second time with 2% bleaching clay (Filtrol F-160, BASF, Florham Park, N.J.) for ~6 hours. The metathesized oil is filtered through a bed of CELITE® 545 diatomaceous earth and then rotary evaporated to concentrate.

The metathesized unsaturated polyol ester is then passed through a wipe film evaporator at 180° C. and <0.5 Torr vacuum to remove olefins up to and including C-18 chain lengths. Representative examples are summarized in the table below.

| Example | Starting unsaturated polyol ester | Pretreated Oil (g) | Catalyst[a] (g) | Max Temperature (° C.) | Max Vacuum (Torr) |
|---|---|---|---|---|---|
| 3A | High erucic acid rapeseed oil | 500 | 0.25 | 61 | 7.9 |
| 3B | Blend of High erucic acid rapeseed oil and canola oil, 50/50 by weight | 500 (250 g HEAR oil and 250 g canola oil) | 0.25 | 61 | 7.9 |
| 3C | High oleic soybean oil | 500 | 0.25 | 61 | 7.9 |

[a]Tricyclohexylphosphine [4,5-dimethyl-1,3-bis(2,4,6-trimethylphenyl)imidazol-2-ylidene] [2-thienylmethylene]ruthenium (II) dichloride [1190427-50-9] available as Cat-METium RF-3 from Evonik Corporation, Parsippany, NJ.

Example 4

Hydrogenations are performed in a T316 stainless steel, 600 ml Parr reactor (Model Number 4563) containing internal cooling coils and a stir shaft with 2 impellers comprised of 4 blades each.

The metathesized unsaturated polyol ester (approximately 200 g) is dissolved in hexanes (120 ml, [110-54-3], EMD, Billerica Ma). To this solution is added a slurry of Nickel on Silica (20 g, [7440-02-0], Catalog #28-1900, Strem Chemicals, Inc., Newburyport, Mass.). The slurried mixtures is transferred via vacuum to the Parr reactor. The mixture is degassed with several vacuum/nitrogen fill cycles. Then with stirring (800-900 rpm), hydrogen gas (550-650 psig, [1333-74-0], UHP grade, Wright Brothers, Inc., Montgomery, Ohio) is charged to the reactor. The reaction is heated at 150° C. and hydrogen gas pressure reduction monitored until constant (~12 hours).

The reaction is cooled to 60° C. and drained from the reactor. The reactor is rinsed with methyl tert-butyl ether ([1634-04-4], EMD, Billerica, Mass.) and combined with the solid hydrogenated metathesized polyol ester. A hot filtration is then performed to remove the catalyst, followed by vacuum to remove all residual solvent. Fully hydrogenated materials are obtained using the method above. Lower hydrogenation levels are obtained by decreasing the reaction temperature to 125 degrees Celsius using 5 grams of catalyst and reducing the reaction time and hydrogen consumed. Iodine Value (IV) is measured, as described elsewhere.

Example 5

The metathesis monomers, dimers, trimers, tetramers, pentamers, and higher order oligomers from the product in Example 2 are fully separated by SFC using the method described above. The individual SFC fractions are collected and trimers, tetramers, and higher order oligomers are combined. The oligomer index of this sample is about 1.

Exemplified Compositions

Examples

| III Composition examples Ingredient | Example 1 % w/w | Example 2 % w/w | Example 3 % w/w |
|---|---|---|---|
| Deionised water | Qs | Qs | Qs |
| Carbopol ETD 2020[1] | 0.500 | — | — |
| Ultrez 21[1] | — | — | 0.40 |
| Sepigel 305[2] | — | 2.0 | — |
| DMDM Hydantoin and butyl carbamate | 0.400 | 0.400 | 0.3 |
| Glycerine | 1.000 | 1.000 | 1.0 |
| Panthenol | 0.500 | 0.500 | 1.0 |
| Disodium EDTA | 0.250 | 0.250 | — |
| Perfume | 0.150 | 0.150 | 0.0 |
| Metathesized unsaturated polyol ester | 0.5 | 2.0 | 1.0 |
| Silwet L7210[3] | 0.5 | 0.24 | 0.8 |
| PEG 45M[4] | — | 0.64 | 0 |
| Triethanolamine | 0.680 | 0.680 | — |
| Sodium hydroxide | — | — | 0.17 |
| Iodopropynyl butylcarbonate | — | — | 0.09 |
| Phenoxyethanol | — | — | 0.5 |

Supplied by:
[1]Lubrizol,
[2]Seppic,
[3]Momentive,
[4]Dow Chemicals

This formulation is made as follows: Heat the water and glycerine while stirring (at about 200 rpm) to 55° C. Then add the disodium EDTA and PEG45M if present and continue stirring at 55° C. until it is fully dissolved. Then add and carefully disperse the thickener (Carbopol, Ultrez, Sepigel) while stirring (at about 250 rpm). Remove from the heat and add the triethanolamine or sodium hydroxide if required and continue to stir at 200 rpm. Then add the panthenol while continuing to stir at 200 rpm. When the temperature reaches 45° C., add the preservatives and continue to stir for 5 minutes. Lastly, add the Silwet L7210, the metathesized unsaturated polyol ester and perfume and continue stirring for about 5 minutes, followed by 1 minute of high shear (at about 7500 rpm).

| Ingredient | Example 4 % w/w |
|---|---|
| Sodium laureth sulphate (25% w/w active) | 22.0 |
| Glycerin | 3.0 |
| Cocamidopropylbetaine | 2.7 |
| Carbopol Ultrez 20 | 1.5 |
| 10% w/w sodium hydroxide solution | 0.78 |
| Metathesized unsaturated polyol ester | 1.0 |
| Silwet L7210 | 0.5 |
| Phenoxyethanol | 0.5 |
| Benzophenone 4 | 0.14 |
| Disodium EDTA | 0.1 |

| Ingredient | Example 4<br>% w/w |
|---|---|
| Methylchloroisothizoline and methylisothiazoline (Kathon CG) | 0.03 |
| Water | q.s. |

The above example 4 is prepared as follows: Dissolve the benzophenone and sodium hydroxide in an appropriate amount of water to aid manufacture. Add water and glycerin and agitate gently. Then add and carefully disperse the thickener (Carbopol) while stirring (at about 250 rpm). Slowly add the sodium laureth sulphate and benzophenone 4 premix. Next add the cocamidopropylbetaine, Kathon CG, metathesized unsaturated polyol ester and Silwet. Add the sodium hydroxide premix and continue to mix until fully homogeneous.

| Ingredient | Ex. 5<br>(% w/w/) | Ex. 6<br>(% w/w/) | Ex. 7<br>(% w/w/) |
|---|---|---|---|
| Phase A | | | |
| Water | 8.00 | 16.00 | 12.00 |
| Brij 35 (Laureth-23) | 2.00 | 4.00 | 3.00 |
| Phase B | | | |
| Petrolatum White | 12.00 | — | — |
| Metathesized unsaturated polyol ester | 3.00 | 9.00 | 15.75 |
| Petrolatum (G2218) | — | 21.00 | 6.75 |
| Phase C | | | |
| Water | 59.81 | 36.81 | 45.76 |
| Brij 35 (Laureth-23) | 4.40 | 4.40 | 4.40 |
| Oleth-10 | | | 3.00 |
| Glycerin | 5.00 | 5.00 | 5.00 |
| Natrosol 250 HHR Hydroxyethylcellulose) | 0.50 | 0.50 | 0.50 |
| PEG-90M (Polyox Wsr-301) | 0.20 | 0.20 | 0.20 |
| Sepigel 305 (Polyacrylamide & C13-14 Isoparaffin & Laureth-7) | 1.60 | 1.30 | 1.55 |
| Phase D | | | |
| Fragrance | 2.50 | 0.80 | 1.10 |
| Disodium EDTA | 0.10 | 0.10 | 0.10 |
| Glydant 55 (DMDM Hydantoin) | 0.30 | 0.30 | 0.30 |
| Glycacil L (Iodopropynyl Butylcarbamate) | 0.09 | 0.09 | 0.09 |
| Phenoxetol (Phenoxyethanol) | 0.50 | 0.50 | 0.50 |
| TOTAL | 100 | 100 | 100 |

The above Examples 5-7 are made according to the method below.
1. Weigh out water from Phase C into a vessel sufficient to hold the entire batch and heat to above 60 C while mixing. Add remaining materials while allowing for sufficient mixing, melting, dispersion and/or incorporation between each addition to form a uniform mixture.
2. Weigh out the water from Phase A into a separate vessel and heat contents to above 60 C while mixing.
3. Add remaining materials from Phase A and mix until fully melted and dissolved.
4. Weigh out the materials from Phase B into a separate vessel and heat contents to above 60 C while mixing.
5. Apply high-shear to Phase A using homogenizer/mill while slowly adding the contents of Phase B to the vessel containing Phase A. Continue homogenization after the addition has been completed.
6. Stop homogenization of the combined Phases A and B, and add mixture to the vessel containing Phase C.
7. Begin cooling batch to below 45° C. while continuing to mix.
8. Once below 45° C., add the materials in Phase D in succession and continue mixing.
9. Cool to below 30° C. and QS with water.

As used herein, molecular weights (mol·wt·s) are provided in unified atomic mass units, daltons, or g/mol. It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein. Similarly, it should be understood that each feature of the each specified embodiment of the invention may be independently applied to each other specified embodiment, as if all such combinations were expressly written herein, unless these combinations are specifically excluded or the relevant features are innately incompatible (e.g. the features are directly contradictory).

All parts, ratios, and percentages herein, in the Description, Examples, and Claims, are by weight of the composition and all numerical limits are used with the normal degree of accuracy afforded by the art, unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

What is claimed is:

1. A composition dispensing hair removal device, said device comprising a composition comprising from 10% to 20% by weight of a metathesized unsaturated polyol ester which is derived from canola oil, the metathesized unsaturated polyol ester having the following properties: (i) a weight average molecular weight of from 5,000 Daltons to 50,000 Daltons; (ii) a free hydrocarbon content, based on total weight of said metathesized unsaturated polyol ester, of from 0.5% to 4%; and (iii) an iodine value of from 30 to 200.

2. The device according to claim 1, wherein said metathesized unsaturated polyol ester has an oligomer index from 0.001 to 1.

3. The device according to claim 1, wherein said free hydrocarbon content is from 0.5% to 3%.

4. The device according to claim 1, wherein the metathesized unsaturated polyol ester is metathesized at least once.

5. The device according to claim 1, wherein said composition further comprises a water soluble polymer.

6. The device according to claim 5, wherein said water soluble polymer is selected from polyethylene oxide, polyvinyl pyrrolidone, polyacrylamide, polyhydroxymethacrylate, polyvinyl imidazoline, polyethylene glycol, polyvinyl alcohol, polyhydroxyethymethacrylate, guars, celluloses, modified celluloses and mixtures thereof.

7. The device according to claim 5, wherein said water soluble polymer is polyethylene oxide having an average molecular weight of between 300,000 and 3 million.

8. The device according to claim 1, wherein said composition further comprises from 0.1% to 8% by weight of a lubricating material of a copolymer of polyethylene oxide and polypropylene oxide.

9. The device according to claim 1, wherein said composition comprises from 0.1% to 5% of a thickening agent and at least 30% by weight of water.

10. The device according to claim 1, wherein said device comprises a handle connected to a hair removal head, wherein said handle comprises a cavity for housing said composition disposed within said handle and an actuator adapted to displace said composition from said cavity to a fluid dispensing member.

11. The device according to claim 10, wherein said fluid dispensing member comprises an elongated contact region forming at least one dispensing orifice.

12. The device according to claim 11, wherein said elongate contact region forms a one way valve.

13. The device according to claim 1, wherein said composition comprises from 10% to 16% by weight of said metathesized unsaturated polyol ester.

14. The device according to claim 1, wherein said free hydrocarbon content is 0.5%.

15. The device according to claim 1, wherein said metathesized unsaturated polyol ester comprising said free hydrocarbon content of from 0.5% to 4% is prepared using one or more stripping techniques.

* * * * *